United States Patent [19]
Schulze et al.

[11] Patent Number: 5,846,254
[45] Date of Patent: Dec. 8, 1998

[54] SURGICAL INSTRUMENT FOR FORMING A KNOT

[75] Inventors: Dale R. Schulze, Lebanon; Rudolph Henry Nobis, Mason; Sean P. Conlon, Cincinnati; Saleem Urrehman Qureshi, West Chester, all of Ohio

[73] Assignee: Ethicon Endo-Surgery, Inc., Cincinnati, Ohio

[21] Appl. No.: 947,657

[22] Filed: Oct. 9, 1997

Related U.S. Application Data

[63] Continuation-in-part of Ser. No. 882,506, Jun. 25, 1997, which is a continuation-in-part of Ser. No. 841,962, Apr. 8, 1997, Pat. No. 5,749,898.

[51] Int. Cl.$^6$ ..................................................... A61B 17/04
[52] U.S. Cl. ........................... 606/228; 606/139; 289/1.2; 289/17
[58] Field of Search .................................... 606/148, 139, 606/228; 289/1.2, 12, 17; 112/80.03, 169

[56] References Cited

U.S. PATENT DOCUMENTS

| | | | |
|---|---|---|---|
| 2,012,776 | 8/1935 | Roeder | 128/326 |
| 2,566,625 | 9/1951 | Nagelmann | 128/326 |
| 3,090,386 | 5/1963 | Curtis | 126/334 |
| 5,320,629 | 6/1994 | Noda et al. | 606/139 |
| 5,573,286 | 11/1996 | Rogozinski | 289/12 |

FOREIGN PATENT DOCUMENTS 912619  4/1994  Germany.

OTHER PUBLICATIONS

Raoul Graumont, John Hensel "Enclycopedia of Knots and Fancy Rope Work" Plates 30–49.

Howard T. Sharp, M.D., James H. Dorsey, M.D., John D. Chovan, Ph.D., P.E., Patrice M. Holtz, R.N. "A Simple Modification to Add Strength to the Roeder Knot" pp. 305–307 Feb. 1996, vol. 3, No. 2 from *The Journal of the American Associates of Gynecologic Laparoscopists*.

Mike Kozminski, M.D., William H. Richards, III, M.D. "Fly–Casting Method of Intracorporeal Laparoscopic Knot Tying", pp. 577–578, from Urology®, Oct. 1994, vol. 44, No. 4.

(List continued on next page.)

*Primary Examiner*—Michael Buiz
*Assistant Examiner*—Tina T. D. Pham
*Attorney, Agent, or Firm*—Matthew S. Goodwin

[57] ABSTRACT

A surgical instrument for forming a fully tied knot to fasten bodily tissue is disclosed. The instrument has a handle assembly for actuating first and second actuators. The first actuator remotely effects movement of a grasping jaw from an open position to a closed position relative to a suture cartridge contained in a cartridge carrier at the distal end of the instrument. Accordingly, the first actuator is capable of causing the manipulation of bodily tissue or suture filament contained in the suture cartridge. The second actuator is operatively connected to the suture filament in the suture cartridge. A portion of the suture filament is configured into a partially tied knot, and when the second actuator is actuated, it causes the proximal end of the filament to be pulled for converting the partially tied knot into a fully formed knot. Consequently, the instrument is particularly desirable during endoscopic surgery where the bodily tissue and the suture filament need to be manipulated remotely, and the conversion of the partially tied knot into the fully formed knot must also be carried out remotely to fasten the targeted tissue.

12 Claims, 31 Drawing Sheets

OTHER PUBLICATIONS

J. L. Pennings, T. Kenyon, L. Swanstrom "The knit stich" from *Surgical Endoscopy* (1995) 9:537–540.

Harry Reich, M.D., H. Courtenay Clarke, M.D., Lisa Sekel, CST "Instruments & Methods", from *Obstet Gynecol* 1992;79:143–147.

Nathaniel J. Soper, M.D., FACS, and John G. Hunter, M.D., FACS "Suturing and Knot Tying in Laparoscopy" *Surgical Clinics of North America*, Oct. 1992 pp. 1139–1153.

S. Kitano, M.D., T. Yoshida, M.D., T. Bandoh, M.D., K. Shuto, M.D., K. Nakashima, M.D. & M. Kobayashi, M.D., "Knot tying intracorporeally at laparoscopic surgery facilitated with newly designed forceps" © 1996 *Blackwell Science Ltd*.

Howard T. Sharp, M.D., James H. Dorsey, M.D., John D. Chovan, Ph.D., P.E., Patricia M. Holtz, R.N., M.S. "The Effect of Knot Geometry on the Strength of Laparoscopic Slip Knots", *Obstetrics & Gynecology*, 1996, pp. 88:408–411.

John E. Meilahn, M.D., "The Need for Improving Laprooscopic Suturing and Knot–Tying", *Journal of Laparoendoscopic Surgery*, vol. 2, No. 5, 1992, pp. 267–268.

D.D. Gaur M.S. FRCS(Eng), "Manual laparoscopic suturing and knot tying made easy", ©1996 Blackwell Science Ltd, pp. 29–33.

Resad Pasic, M.D., Ph.D., Ronald L. Levine, M.D., "Laparoscopic Suturing and Ligation Techniques", Nov. 1995, vol. 3, No. 1 *The Journal of the American Association of Gynecologic Laparoscopists*, pp. 67–79.

Sung–Tao Ko and Mohan C. Airan, "Therapeutic laparoscopic suturing techniques", *Surgical Endoscopy*, (1992)6:41–46.

Thierry Vancaillie, M.D., Ernst H. Schmidt, M.D., "Therapeutic Laparoscopy", from *The Journal of Reproductive Medicine* pp. 891–894.

Zoltan Szabo, Ph.D., FICS, and George Berci, M.D., FACS, FRCS ed (Hon), "Extracorporeal and Intracorporeal Knotting and Suturing Techniques" *Gastrointestinal Endoscopy Clinics of North America*, pp. 367–373.

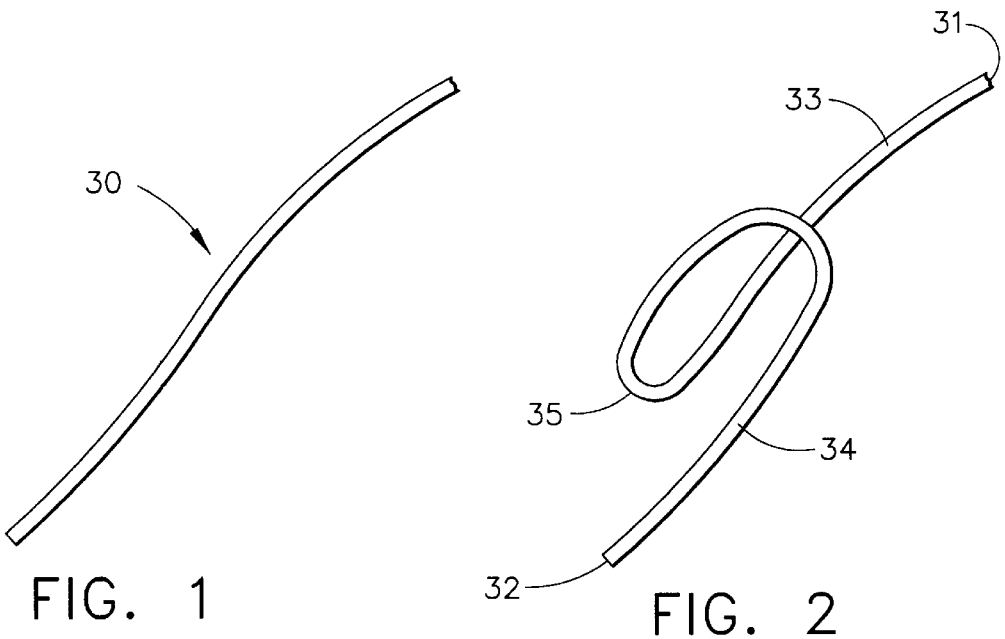
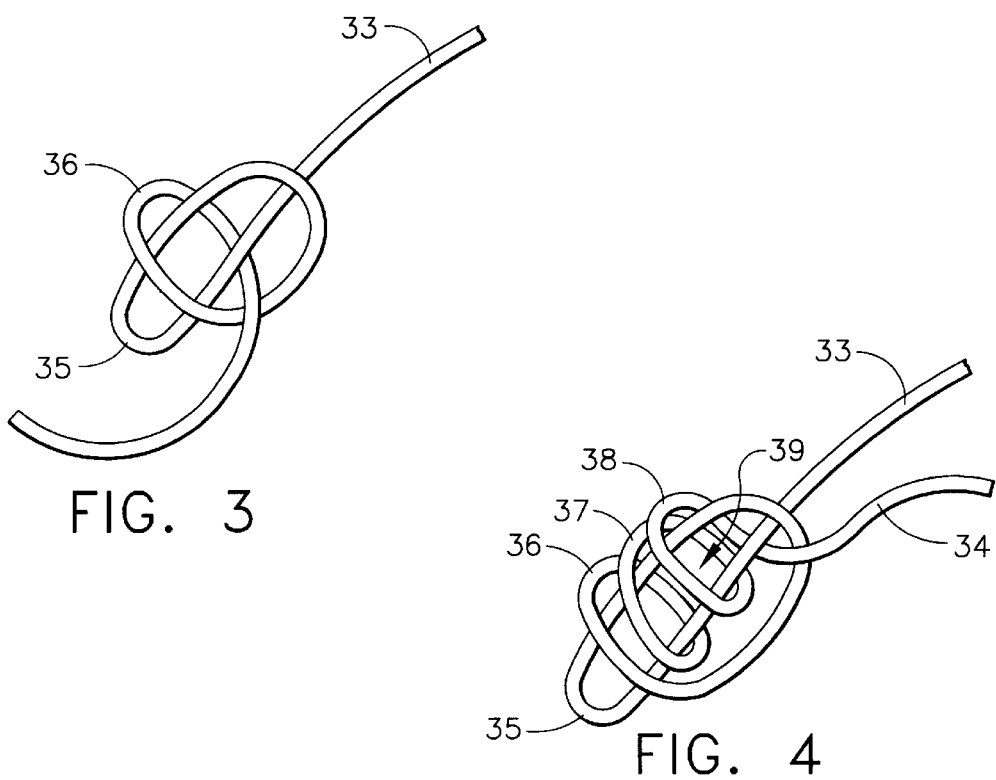
FIG. 1
FIG. 2
FIG. 3
FIG. 4

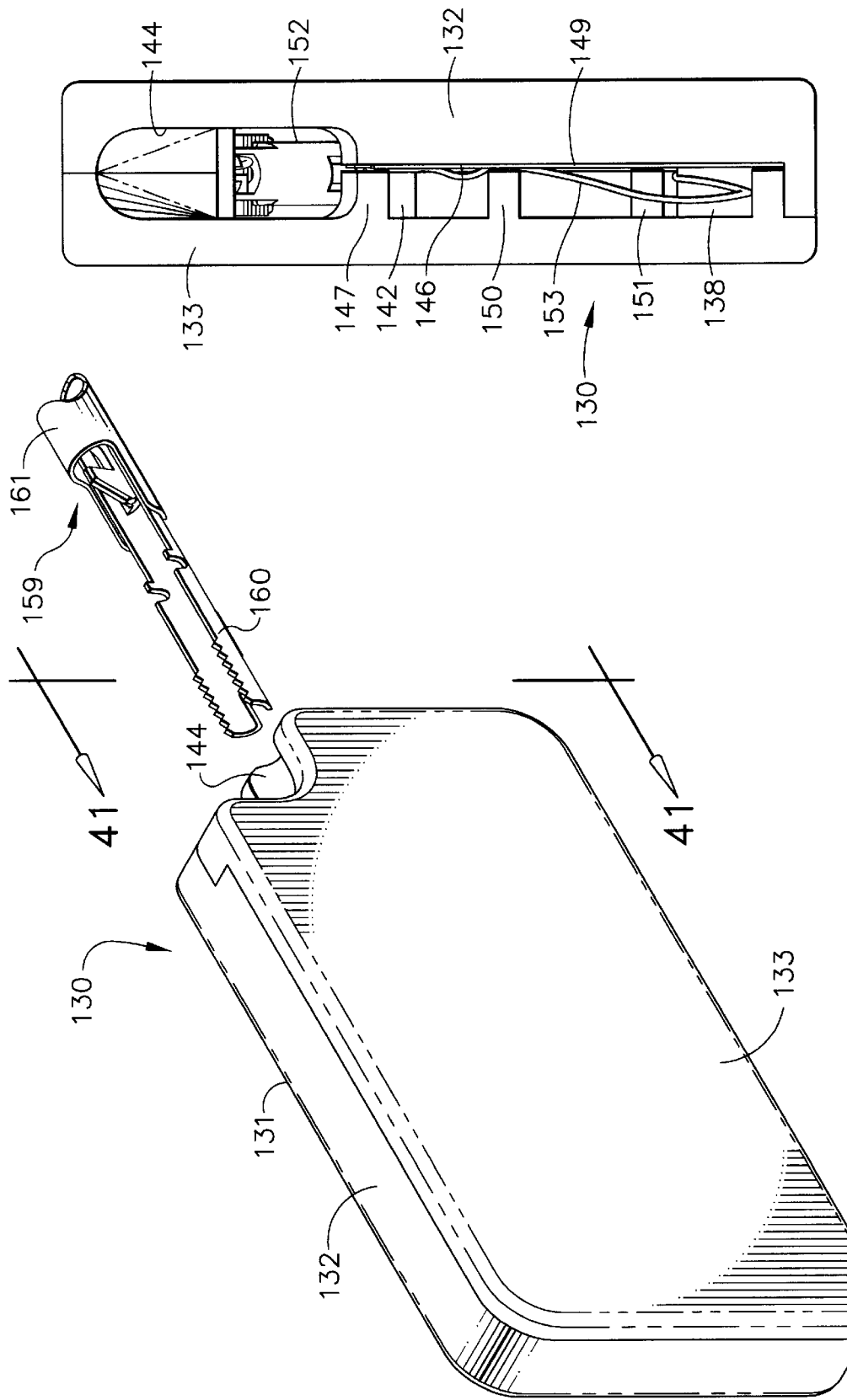

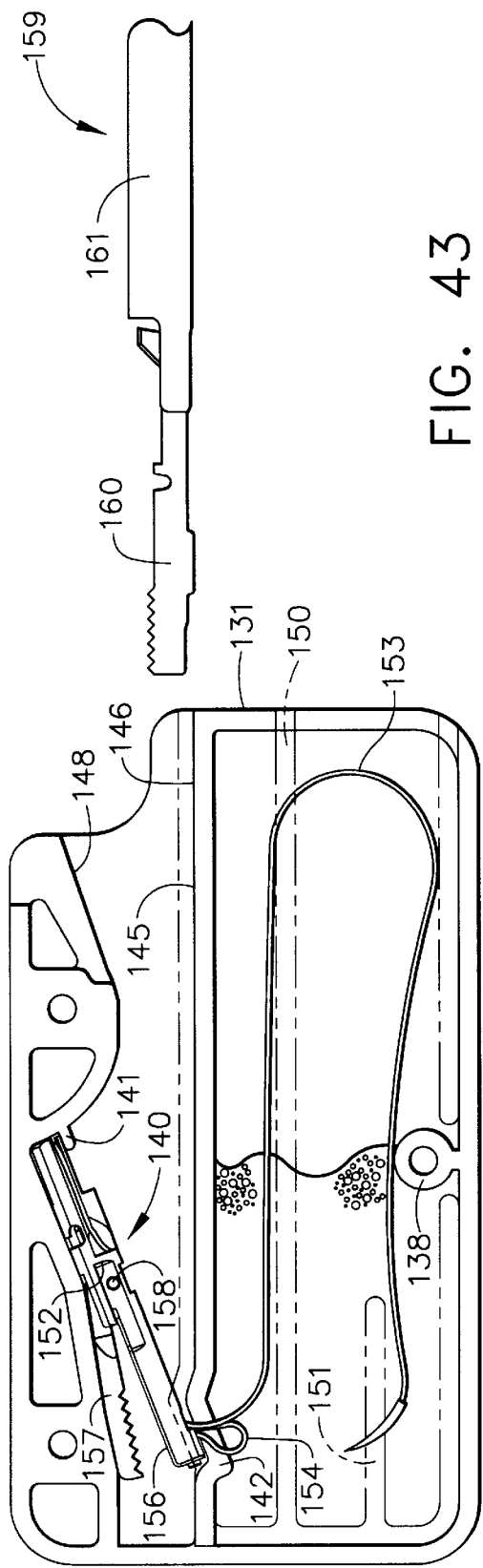
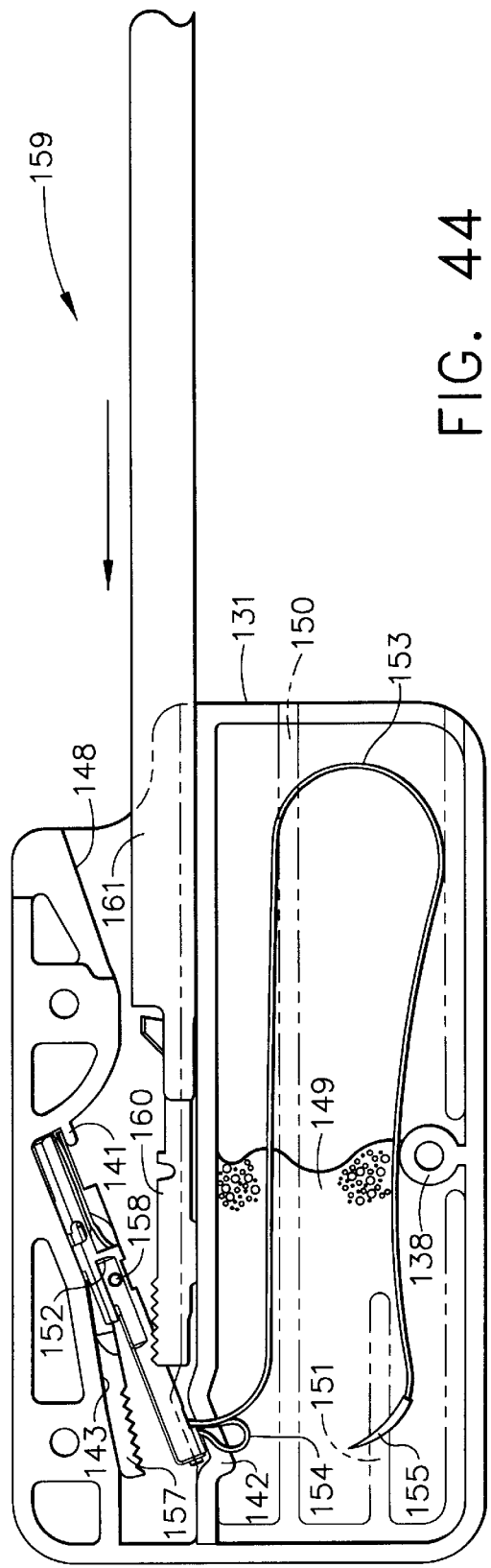

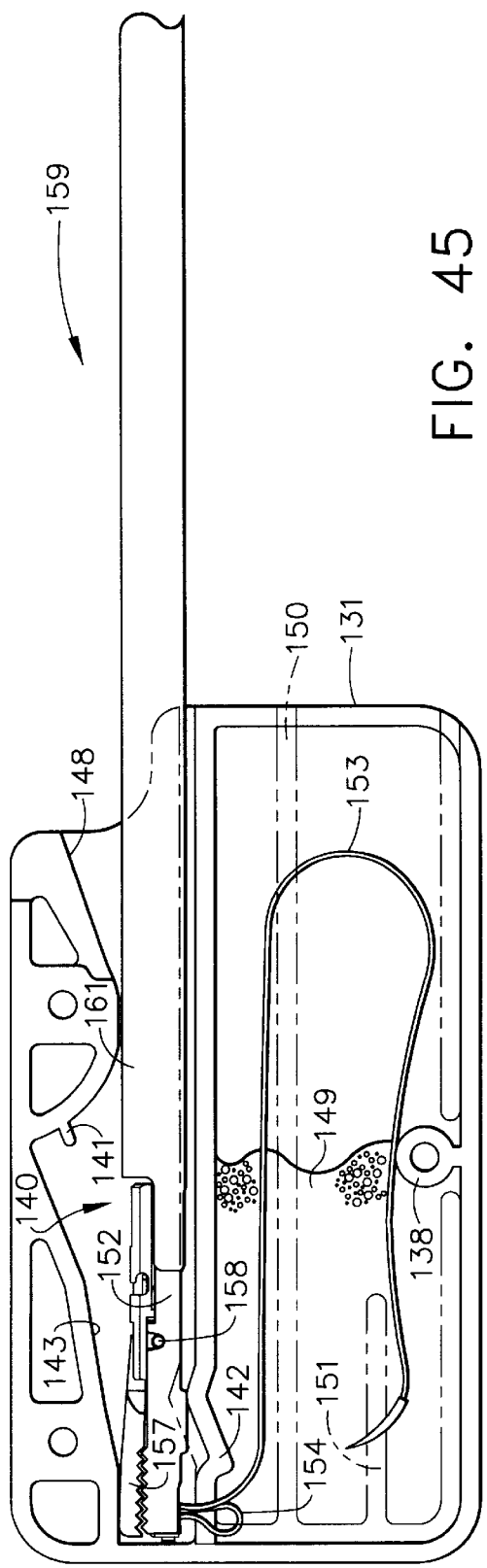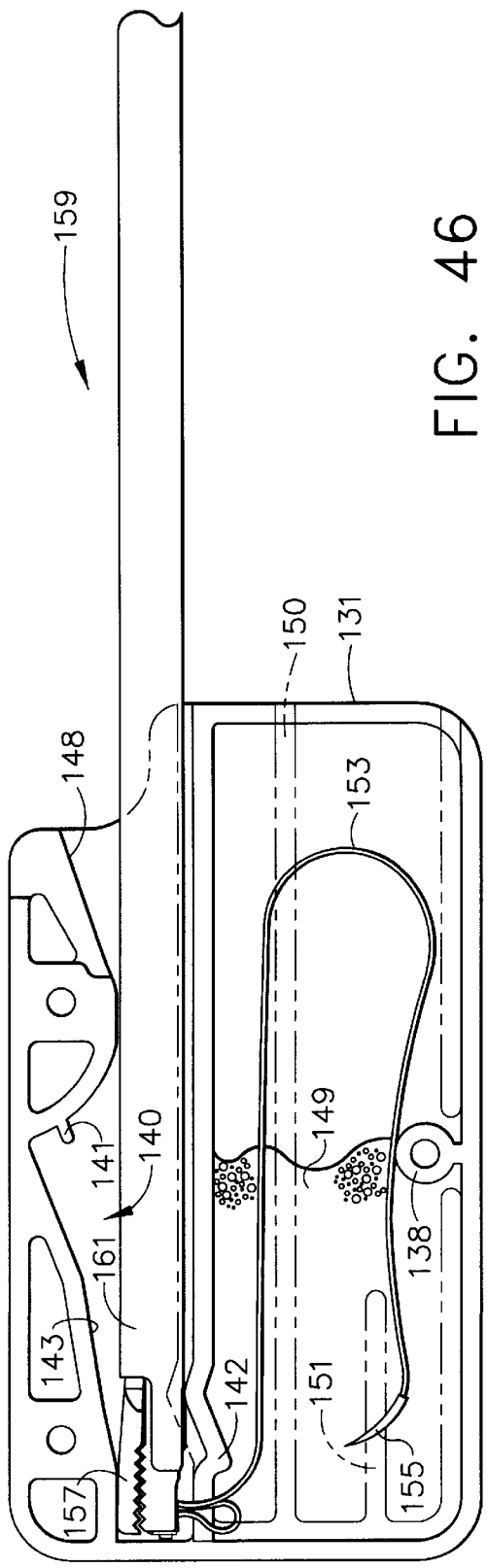

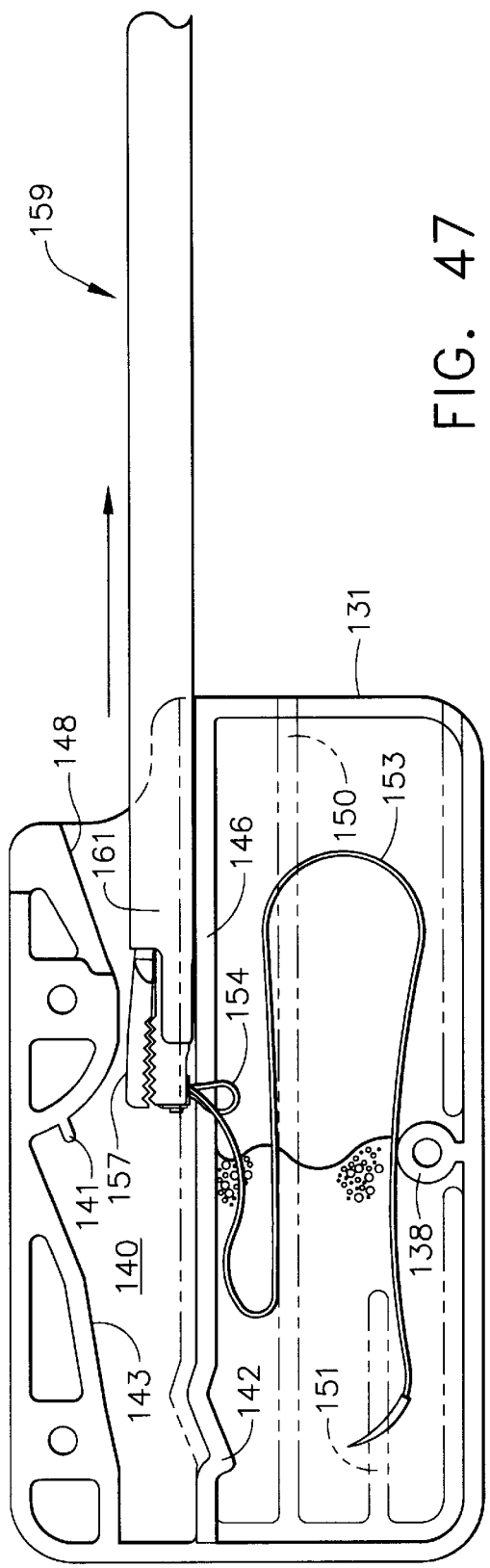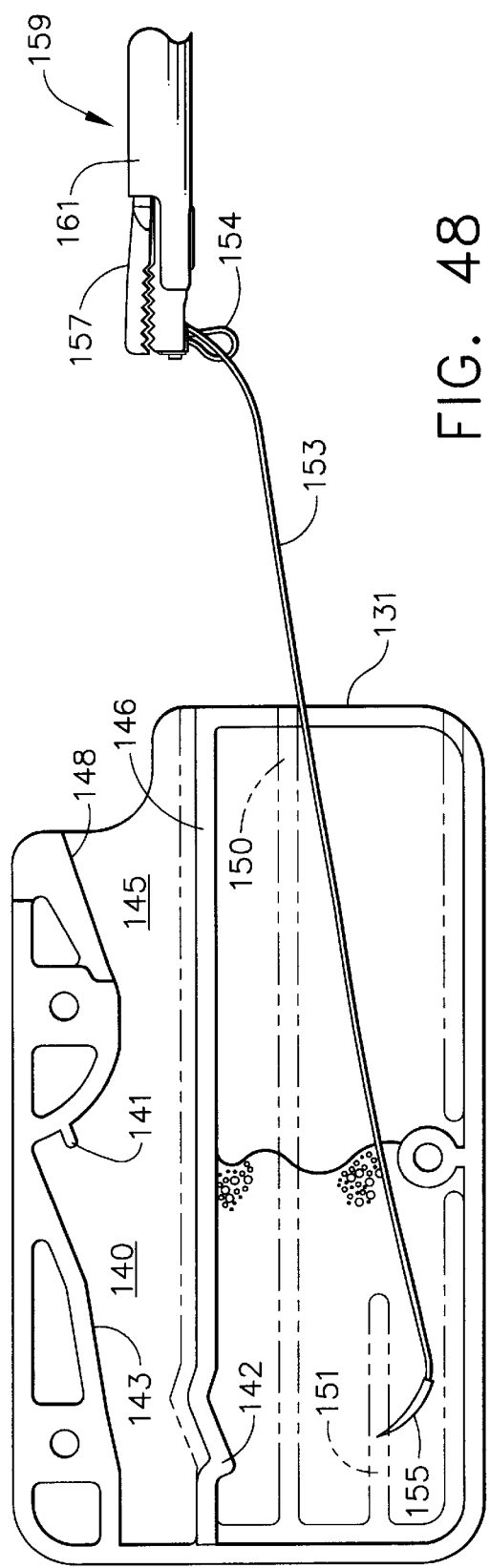

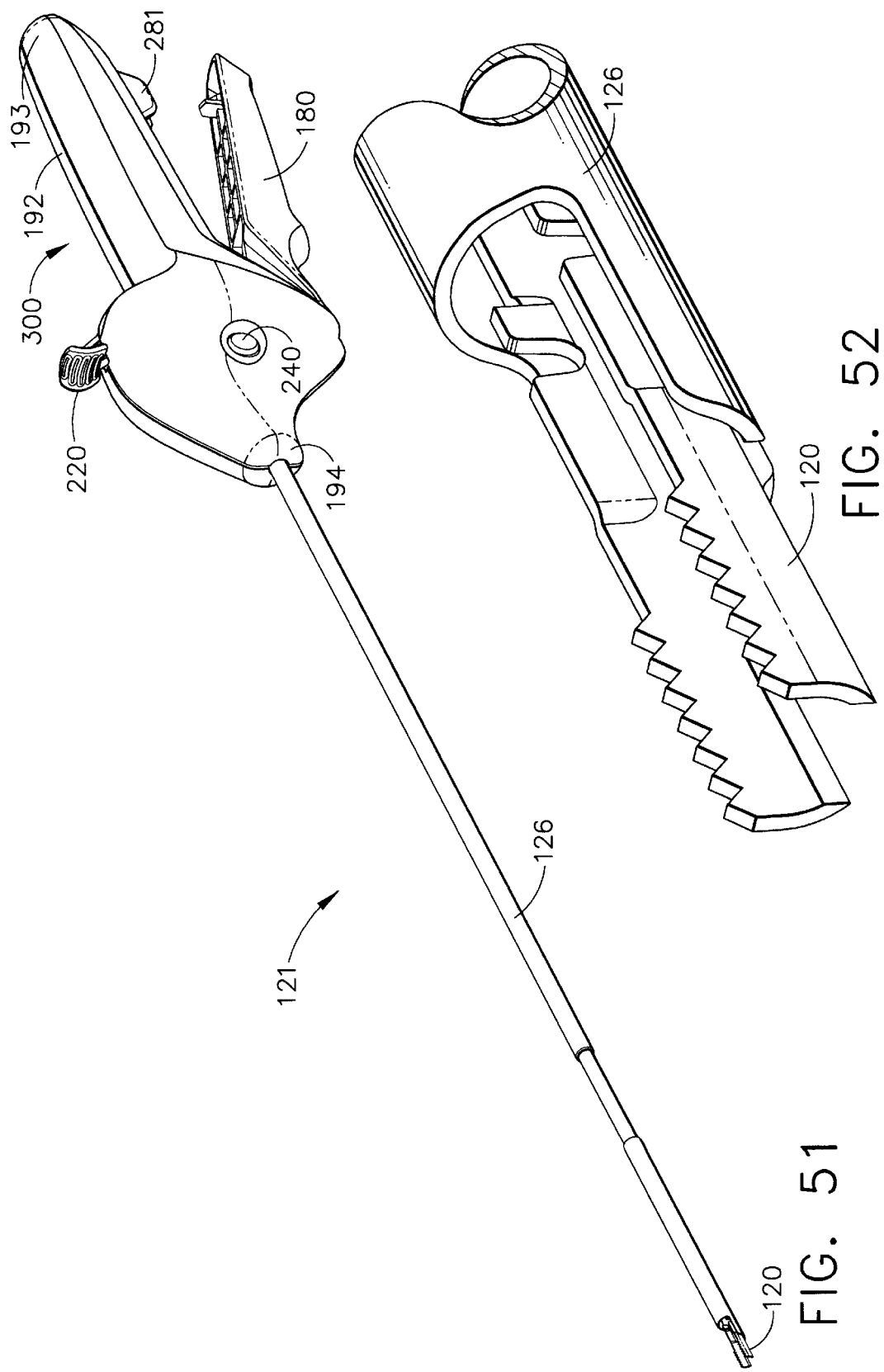

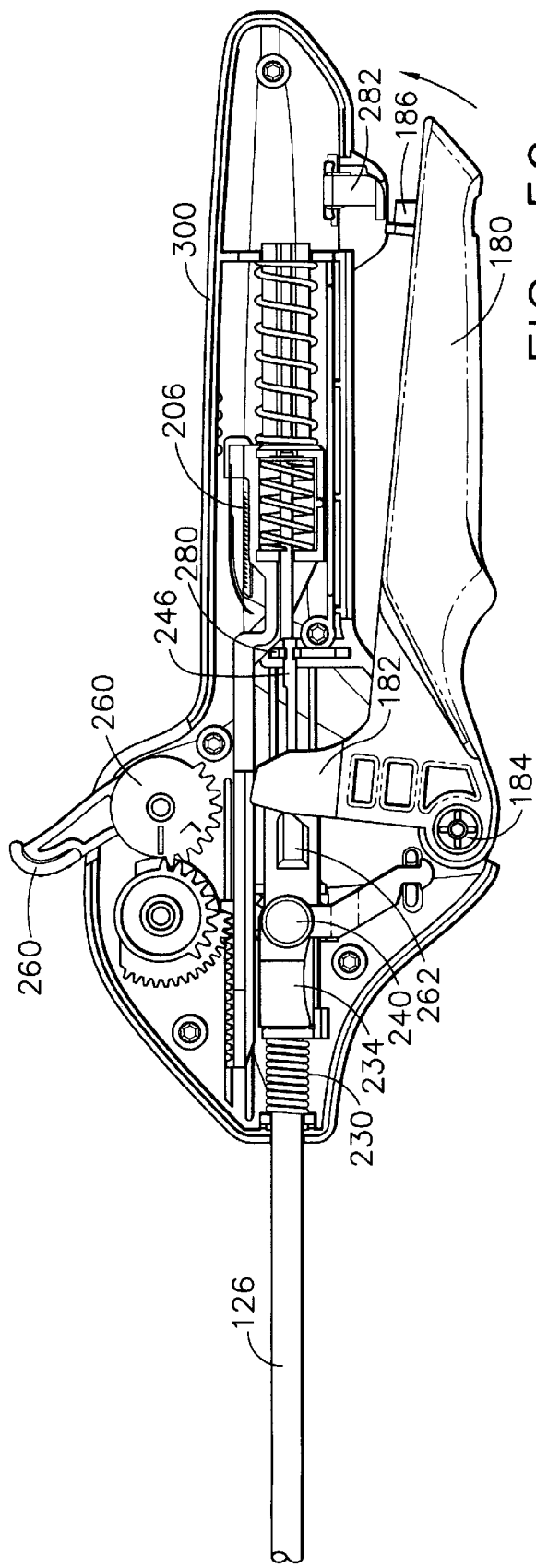
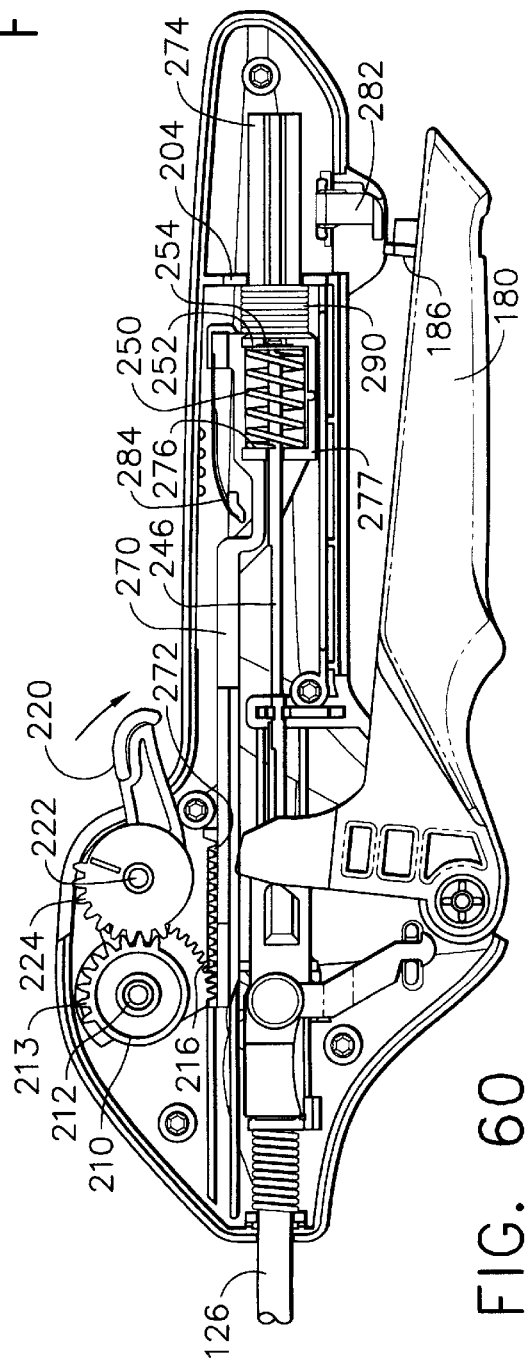

SURGICAL INSTRUMENT FOR FORMING A KNOT

This is a continuation-in-part of Ser. No. 08/882,506, filed Jun. 25, 1997, which is a continuation-in-part of Ser. No. 08/841,962, filed Apr. 8, 1997, now U.S. Pat. No. 5,749,898, each of which is incorporated by reference herein.

BACKGROUND OF THE INVENTION

This invention relates to a surgical instrument for facilitating the placement of a surgical knot made from a suture filament. In particular, the invention relates to such an instrument which is particularly adapted for deployment of the knot during minimally invasive surgical procedures where access to the surgical site is limited.

A mainstay of surgical practice has been and will continue to be the formation and placement of surgical knots from suture filament to fasten tissue during an operative procedure. Numerous surgical knots have been developed over an appreciable period of time, and the art of forming and tying knots for surgical applications is a critical skill which a surgeon must possess to perform an operation safely and efficiently. Accordingly, the art is extensively developed. See, for example, Tissue Approximation in Endoscopic Surgery, Alfred Cuschieri, Zoltan Szabo, Times Mirror International Publishers, 1995, which describes numerous surgical knots made from suture filament to facilitate the approximation of tissue during surgery.

The art of surgical knots is also well represented in the patent literature. U.S. Pat. No. 2,012,776 discloses a surgical instrument for facilitating the placement of various forms of slip knots made from surgical filament. The inventor named on the '776 patent, H. A. Roeder, developed the "Roeder Knot" which is a surgical knot which is frequently used in practice today. More recently, U.S. Pat. No. 5,573,286 discloses a surgical knot of suture strand particularly adapted for orthopedic applications. The preferred embodiment described in the '286 patent is directed to tying the knot to a bone.

Early on, it was recognized that the deployment and placement of surgical knots within a remotely accessible surgical site could be difficult, cumbersome and often unreliable. Accordingly, instrumentation was developed to facilitate the placement of knots in remote locations. Cleverly, a pre-tied knotted loop of suture was often used to reduce the number of steps required to form the tightened knot. For example, U.S. Pat. Nos. 2,566,625 and 3,090,386 describe surgical devices which are adapted to support a pre-tied knotted loop of suture for suturing or ligating tissue, particularly during procedures where the tissue desired to be manipulated is difficult to access.

More recently, instrumentation has been developed for facilitating the placement of knots particularly during minimally invasive surgical procedures. In particular, U.S. Pat. No. 5,320,629 discloses the formation of a pre-tied knotted loop of suture, and the placement of the pre-tied knotted loop on a surgical device for facilitating the tightening of the loop to approximate tissue during endoscopic surgical procedures. German Patent No. 912619 also discloses a device similar to that disclosed in the '629 patent.

Although the art of surgical knots is well developed, and surgical devices for facilitating the placement of tightened knots from a pre-tied knotted loop of suture have also been developed for application at remote surgical sites, there are problems which still need to be addressed. In particular, in those surgical procedures where access to the site is limited, for example during minimally invasive procedures such as endoscopic surgical procedures, the knots can be difficult to deploy. Frequently, the knots which can be deployed are routinely slip knots having poor knot security. If knot security is poor, then the approximated tissue may not be held for a sufficient period of time to promote adequate wound healing. Additionally, during minimally invasive procedures, the pre-tied knotted loops of suture which have been described in the prior art devices can be difficult to efficiently tighten for final deployment.

Therefore, in minimally invasive surgical procedures where access to the surgical site is limited, what is needed is an assembly for facilitating the formation of a surgical knot. The assembly should be relatively simple in construction and should be compatible with a partially tied surgical knot. The assembly should facilitate the conversion of the partially tied knot into a fully formed knot which can provide a consistently strong knot security each time the knot is placed to enable even an inexperienced surgeon to confidently and efficiently place a secure suture knot. Additionally, it would be desirable if it were possible to easily retrofit the assembly onto various surgical instruments, particularly endoscopic instruments, for ease of use of the assembly to place surgical knots. Finally, it would be helpful if it were possible to reload the assembly with a second partially tied knot following deployment of the first knot so that the assembly can be used to place multiple knots.

In addition, what is needed is a device to facilitate the loading of a suture cartridge assembly onto a surgical instrument. Specifically, what would advance the state of the surgical art would be a device which aids the surgeon to load the assembly onto a surgical instrument for deploying a surgical knot from the suture filament contained in the assembly, and to easily reload the instrument with a second suture cartridge assembly after the first spent assembly has been removed from the instrument. It would also be advantageous if such a device could be designed to avoid the need for the user to handle a needle when attached to the filament and to be a suitable container for shipping and storage of the suture cartridge when used in conjunction with the other packaging materials.

Further, it would be highly desirable if a surgical instrument were provided which can readily form the fully tied knot remotely, particularly during an endoscopic surgical procedure where access to the internal anatomical cavity is severely limited. In particular, it would be desirable if a surgical instrument were provided which had a handle assembly with actuators for remotely manipulating the internal tissue, suture or needle (whatever may be desired) and facilitating the formation of the fully formed knot from the partially tied knot. More specifically, what is needed is a handle assembly which has a first actuator to control the manipulation of the tissue, filament or needle, and a second actuator to control the manipulation of the suture filament for the formation of the fully formed knot.

SUMMARY OF THE INVENTION

The invention is a surgical instrument for forming a fully tied knot to fasten bodily tissue during a surgical procedure. The surgical instrument comprises a suture cartridge, a cartridge carrier, a grasping jaw, a handle assembly and a closure tube.

The suture cartridge of the surgical instrument is located at a distal end of the instrument. The cartridge contains a suture filament configured into a partially tied knot at a distal end of the suture filament.

The cartridge carrier of the surgical instrument is also located at the distal end of the instrument. The cartridge carrier receives the suture cartridge.

The grasping jaw of the surgical instrument faces the suture cartridge in the cartridge carrier. The grasping jaw is moveable from an open position spaced from the suture cartridge to a closed position adjacent the suture cartridge.

The handle assembly of the surgical instrument is spaced from the suture cartridge. It is located at a proximal end of the instrument. The handle assembly has a grip for manipulating the instrument. It also has a first actuator for effecting the movement of the grasping jaw from the open position to the closed position. Further, the handle assembly has a second actuator operatively connected to a proximal end of the suture filament. When the second actuator is actuated, the proximal end of the suture filament is pulled proximally, and the fully tied knot is formed from the partially tied knot to fasten the bodily tissue.

The closure tube of the surgical instrument couples the cartridge carrier to the handle assembly. The closure tube is moveable from a proximal position to a distal position in response to actuation of the first actuator. In its proximal position, the grasping jaw of the instrument is located in its open position. Conversely, when the closure tube is in its distal position, the grasping jaw is in its closed position.

Significantly, the first and second actuators of the handle assembly enable the user to open and close the grasping jaw for grasping the bodily tissue or the filament, and operatively pull the suture filament proximally for forming the fully tied knot, respectively. The surgical instrument of this invention can perform these two highly desirable functions remotely from the handle assembly, thus further facilitating the deployment of a fully tied knot from a partially tied knot endoscopically when direct access to the targeted anatomical structure is severely constrained. The first actuator causes movement of the grasping jaw so that the bodily tissue or suture filament can be appropriately manipulated for the proper placement of the knot. Once this initial manipulation has been performed, the second actuator can subsequently be actuated to convert the partially tied knot into the desired fully formed knot for the fastening of the targeted bodily tissue.

The surgical instrument of this invention can be used in any surgical procedure where it is necessary or desirable to form a fully tied knot from a suture filament to fasten bodily tissue. In a broad sense, the instrument can be used not only in endoscopic procedures but also in conventional open procedures. However, the instrument of this invention is particularly adapted for endoscopic applications where direct access to the targeted tissue is severely limited.

BRIEF DESCRIPTION OF THE DRAWINGS

FIGS. 1–6 are perspective views illustrating the sequence of steps for forming a partially tied knot from a length of suture filament.

FIG. 40 is a perspective view of a preferred load assist device in a cooperative relationship with a cartridge carrier of the preferred surgical instrument of this invention.

FIG. 41 is a proximal end view of the load assist device of FIG. 40.

FIG. 43 is an inside elevation view of the base of the cartridge casing illustrating the placement of the suture cartridge including the suture filament and surgical needle in the base. The cover of the cartridge casing for the load assist device is shown in phantom line. The cartridge carrier of the preferred surgical instrument of this invention is shown in pre-load relationship with the load assist device.

FIG. 44 is a view in side elevation of the interior of the load assist device of FIG. 40 as the cartridge carrier makes contact with the suture cartridge inside the cartridge casing.

FIG. 45 is a view in side elevation of the interior of the load assist device of FIG. 40 illustrating the suture cartridge having been seated onto the cartridge carrier of the preferred surgical instrument of this invention.

FIG. 46 is a view in side elevation of the interior of the load assist device of FIG. 40 illustrating the suture cartridge assembly secured into the cartridge carrier when a closure tube in the preferred surgical instrument is moved forwardly to cover a portion of the suture cartridge.

FIG. 47 is a view in side elevation of the interior of the load assist device of FIG. 40 illustrating the partial withdrawal of the loaded cartridge carrier.

FIG. 48 is a view in side elevation of the interior of the load assist device of FIG. 40 illustrating the further withdrawal of the loaded cartridge carrier.

FIG. 51 is a perspective view of the preferred surgical instrument of this invention as it may be configured for packaging and shipping and when not loaded with a suture cartridge assembly.

FIG. 52 is an enlarged, perspective view of the distal portion of the surgical instrument of FIG. 51.

FIG. 59 is a side elevation of the interior of the handle assembly of the surgical instrument of FIG. 51 in the configuration depicted in FIG. 55.

FIG. 60 is a side elevation of the interior of the handle assembly of the surgical instrument of FIG. 51 in the configuration depicted in FIG. 56.

DETAILED DESCRIPTION OF THE PREFERRED EMBODIMENT

Figure 5:
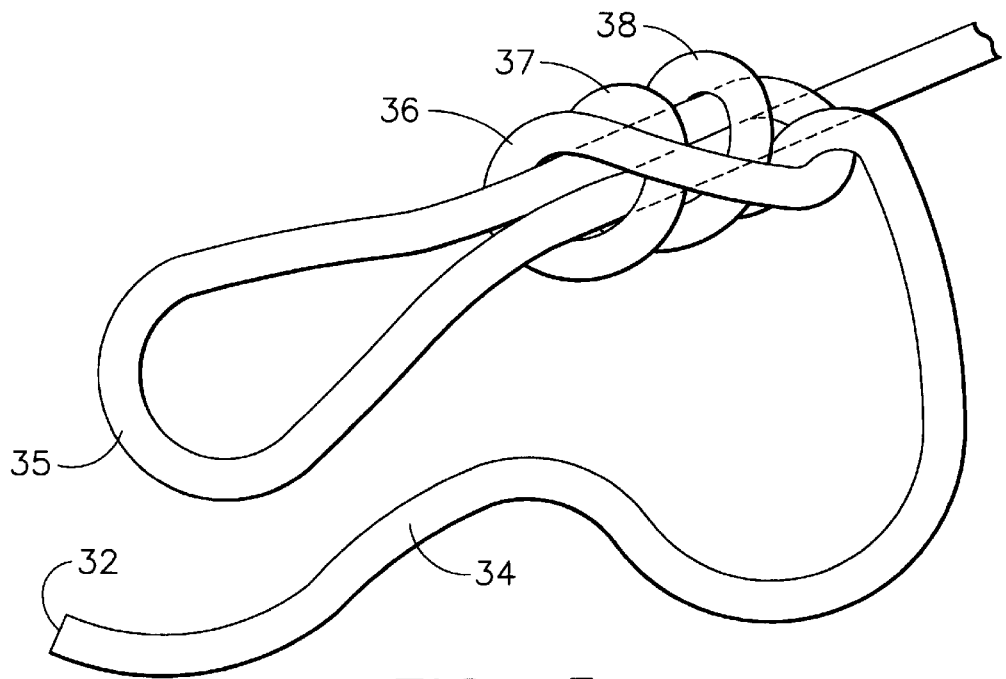

FIGS. 1–6 illustrate how a partially tied surgical knot can be made from a length of suture filament. The partially tied knot thus formed can be used in the practice of the specific embodiments of this invention illustrated hereinafter. Of course, other partially tied knots can be used in the practice of this invention.

The suture filament 30 shown in FIG. 1 can be composed of any suture material currently used or hereafter developed. The suture filament may be a monofilament suture or a multifilament, braided suture. The suture filament, regardless of construction, may be non-absorbable or bio-absorbable, depending on the particular application for which the suture is being used to fasten tissue.

The length of suture filament 30 has proximal and distal ends, 31 and 32, respectively. Adjacent the proximal end, there is a proximal length 33 of suture filament. Correspondingly, adjacent the distal end of the suture filament, there is a distal length 34 of the suture filament.

As shown in FIG. 2, a first loop 35 is formed by manipulating the distal length 34 of the suture filament. Now looking at FIG. 3, while the proximal length 33 of the suture filament remains fixed, the distal length is manipulated to form a second loop 36 wrapped generally transversely around the first loop 35. Third and fourth loops, 37 and 38, respectively, are likewise formed about the first loop as depicted in FIG. 4. The second, third and fourth loops are generally parallel to each other and are oriented generally transversely to the first loop. For purposes of describing this partially tied knot, these loops may be referred to collectively as the "knot loops". The number of knot loops may vary depending on the particular application for which the knot is used. In the illustrated embodiment, the second, third and fourth loops together form a common loop core 39 which receives the first loop 35.

Reviewing FIG. 5, the loosely formed knot is tightened by applying tension on the distal length 34 of the suture filament. In so doing, the second, third and fourth loops tighten down on the first loop, and thus the first loops is securely received in the common loop core.

Figure 6:
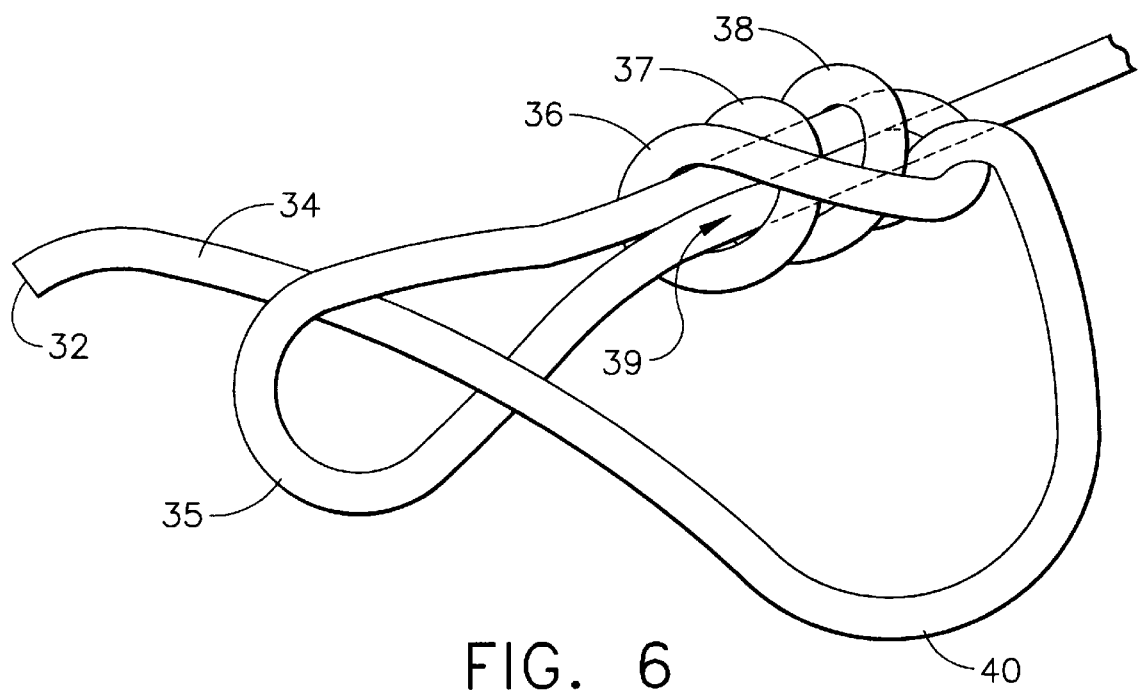

As depicted in FIG. 6, a tissue-fastening loop 40 can be formed by passing the distal end 32 and the distal length 34 of the suture filament through the first loop 35.

Figure 7:
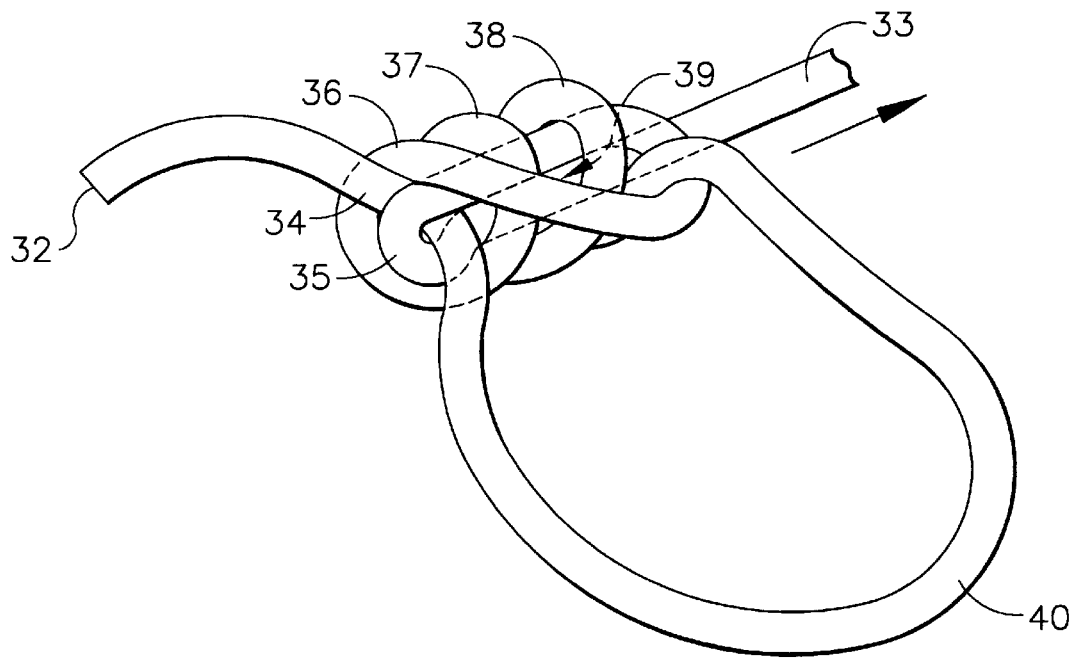
FIGS. 7–8 are perspective views of the steps to convert the partially tied knot depicted in FIG. 6 into a non-slip surgical knot.

To form the knot, the partially tied knot of FIG. 6 is taken, and tension on the proximal length 32 of the suture filament is applied in the proximal direction as indicated by the arrow in FIG. 7. To facilitate forming the knot, the surgeon ideally holds his fingertips against the proximal side of the knot loops while tension is applied to the proximal length 32 of the suture filament. Alternatively, as described in the embodiments below, an instrument can be used to hold the knot loops in place. As tension is applied, the first loop 35 begins to be pulled through the common loop core 39 of the knot. When the first loop has sufficiently diminished in size from that shown in FIG. 6, it snares the distal length 34 of the suture filament. With continuing proximal tension on the proximal length of the suture filament, the first loop and the distal length of filament are pulled through the common loop core 39. When the first loop and distal length of filament emerge from the fourth loop 38, an audible "clicking" sound may alert the user that the completed knot has been formed.

Although the partially tied knot illustrated in FIG. 6, often referred to as a "blood" knot, is the preferred partially tied knot for conversion into the fully formed, non-slip knot which is used in the practice of this invention, other slip knots described in the literature can be used. The key characteristic for the acceptability of other partially tied knots is a common loop core (exemplified in FIG. 6 as common loop core 39) allowing passage of suture filament through the core. See, for example, The Encyclopedia of Knots and Fancy Ropework, R. Graumont and J. Hensel, Fourth Edition, Cornell Maritime Press. Suitable partially tied knots are shown in this book as numbers 102, 185, 227 and 349 on pages 71, 83, 87 and 102, respectively.

Figure 8:
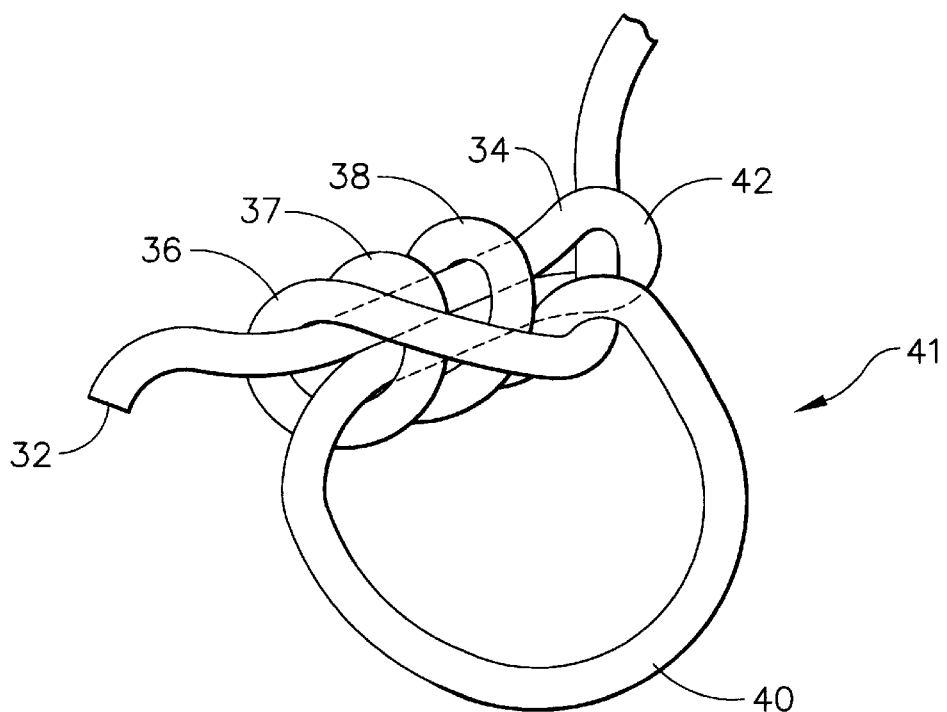

As depicted in FIG. 8, the completed surgical knot is a non-slip knot 41. The first loop has been eliminated, and a distal loop 42 positioned adjacent to the fourth loop 38 is formed from a portion of the distal length of the suture filament. The tissue loop 40, which is used to fasten tissue, consequently becomes rigidly fixed and secure. Tension applied to the loop 40 due to the tendency of the fastened tissue to expand or pull apart may result beneficially in further tightening of the non-slip knot.

Figure 9:
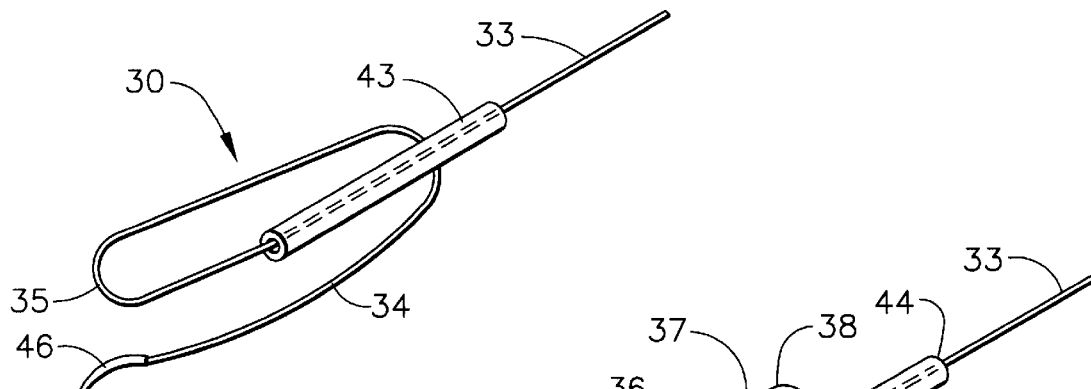
FIGS. 9–10 are perspective views illustrating the formation of the partially tied knot of FIG. 6, which includes a surgical needle attached to the suture filament, about a core tube.
Figure 10:
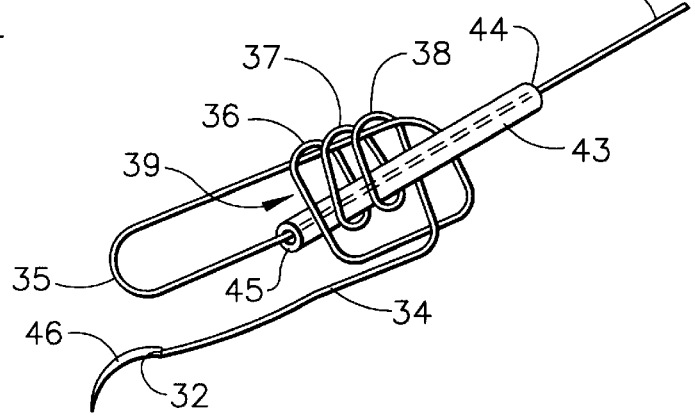

Referring to FIGS. 9 and 10, there is shown the formation of the partially tied knot depicted in FIGS. 1–6, formed about a core tube 43. The core tube facilitates the placement of the partially tied knot adjacent tissue desired to be fastened, as well as the conversion of the partially tied knot into the completed non-slip knot shown in FIG. 8. The core tube has proximal and distal ends, 44 and 45, respectively. A surgical needle 46 is attached to the distal end 32 of the surgical filament. The proximal length 33 of the filament is passed through the core tube. The length of suture filament exceeds the length of the core tube so that the proximal length of the suture filament may extend from the proximal end 44 of the core tube. Additionally, a sufficient amount of suture filament represented by its distal length 34 exits the distal end of the core tube so that it is possible to form the partially tied knot about the distal end 45 of the core tube. The first loop 35 and the subsequent knot loops represented by the second, third and fourth loops, 36, 37 and 38, are formed about the distal end of the core tube. Once formed, tension is applied to the distal length of the filament to tighten the knot loops about the distal end of the core tube.

Figure 11:
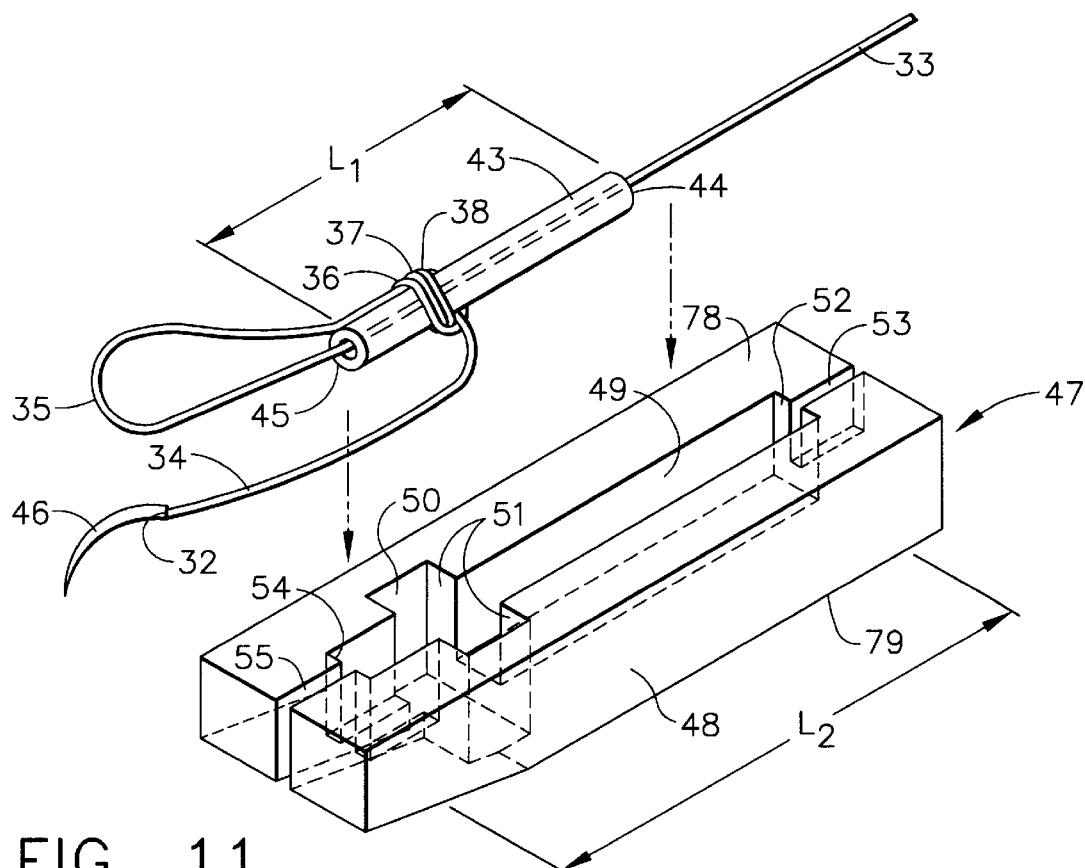
FIG. 11 is an exploded perspective view illustrating the partially tied knot of FIG. 6 formed about the core tube depicted in FIGS. 9–10, in combination with a suture cartridge.

The partially tightened knot formed about the core tube can be loaded into a suture cartridge 47 as illustrated in FIG. 11. The suture cartridge has an elongated body 48. It also has top and bottom faces 78 and 79, respectively. A tube slot 49 for receiving the core tube 43 is embedded in the body of the cartridge between the top and bottom faces. The body also contains a knot recess 50 which has a pair of stripping shoulders 51. Extending from a proximal edge 52 of the tube slot in a proximal direction is a filament slot 53. Correspondingly, extending from a distal edge 54 of the tube slot toward a distal end of the cartridge body is a loop slot 55. The length of the core tube, designated as $L_1$ in FIG. 11, is less than the length of the tube slot, designated as $L_2$ in FIG. 11.

Figure 13:
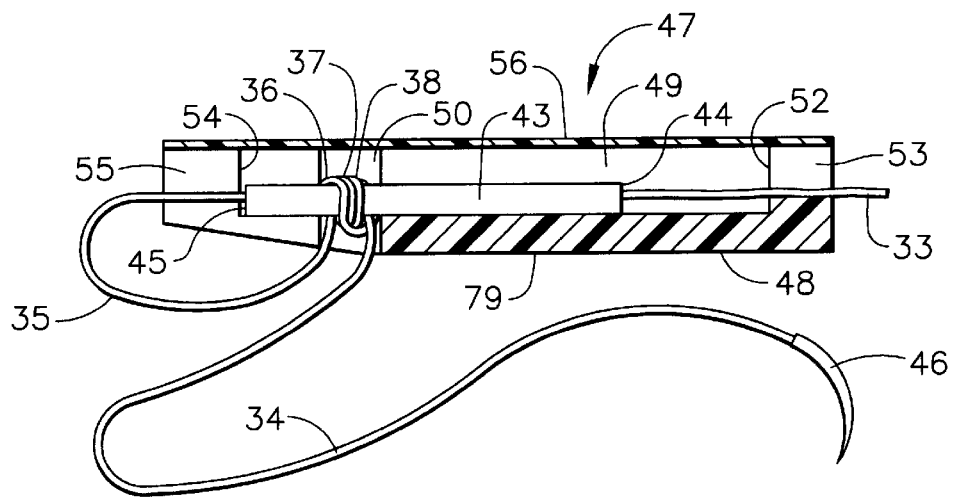
FIG. 13 is a section view of the assembly depicted in FIG. 12 taken along line 13—13 of that Figure.

When the partially tied knot is formed about the core tube 43, the knot loops are wrapped about the distal end 45 of the core tube. The free proximal end of the suture filament extends from the proximal end 44 of the core tube. The first loop 35 of the partially tied knot extends from the distal end of the core tube. When the core tube is loaded into the tube slot 49 of the cartridge body between the top and bottom faces, the knot loops sit inside the knot recess and abut the stripping shoulders of the knot recess. A portion of the proximal length 33 of the suture filament rests in the filament slot 53 embedded in the body of the cartridge, and the remaining portion of the proximal length of the suture filament extends from the proximal end of the cartridge body. Correspondingly, the first loop 35 of the partially tied knot and the distal end 34 of the surgical filament are received in the loop slot 55. A substantial portion of the first loop and the distal length of suture filament descend from the bottom face 79 of the cartridge body. In its original position as best illustrated in FIG. 13, the distal end 45 of the core tube is adjacent the distal edge 54 of the tube slot. Since the tube slot 49 has a length greater than that of the core tube 43, the core tube is capable of sliding proximally toward the proximal edge 52 of the tube slot. In this position, the knot is trapped in recess 50. The surgeon can then easily manipulate needle 46 and suture filament 34 without danger of prematurely deploying the knot.

Figure 12:
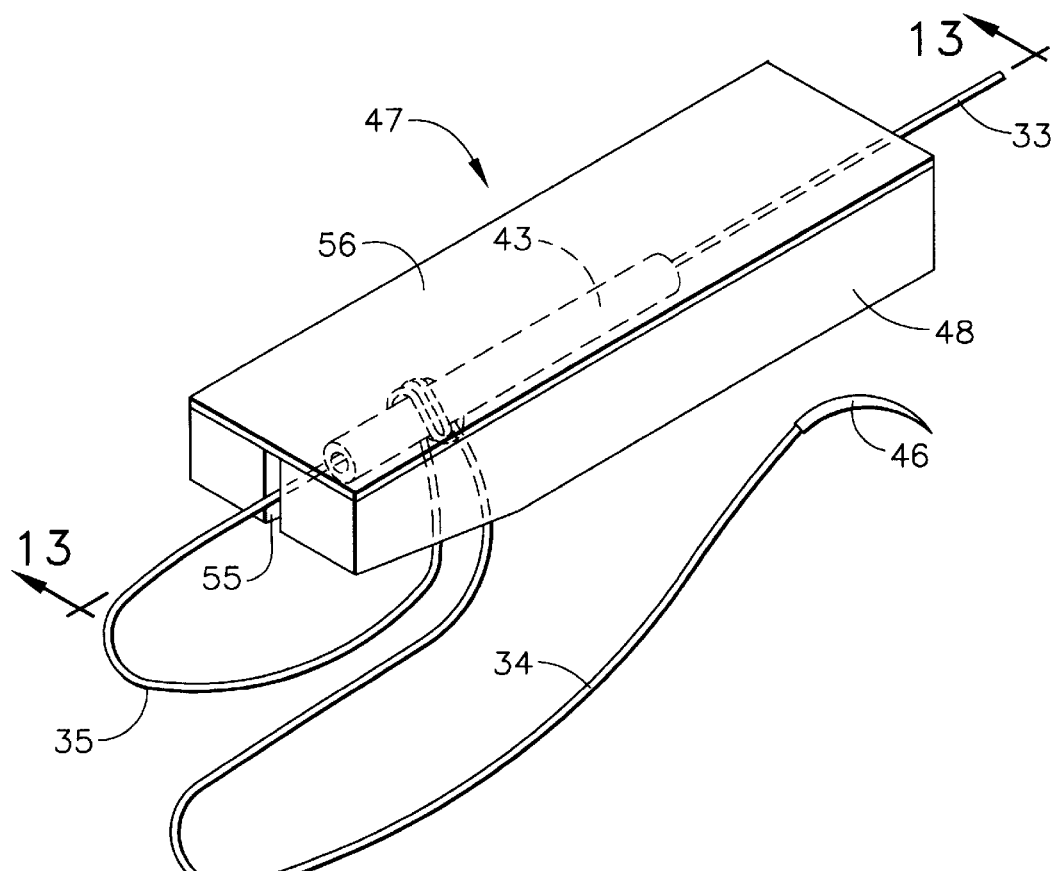
FIG. 12 is a perspective view in assembly of the combination depicted in FIG. 11, where the suture cartridge has a cartridge top.

When the core tube is loaded into the tube slot within the body of the cartridge, a cartridge top 56 can be mounted onto the top face 78 of the cartridge body 48 as shown in FIG. 12. When the cartridge top is mounted, the core tube 43 is fully enclosed within the cartridge.

Figure 14:
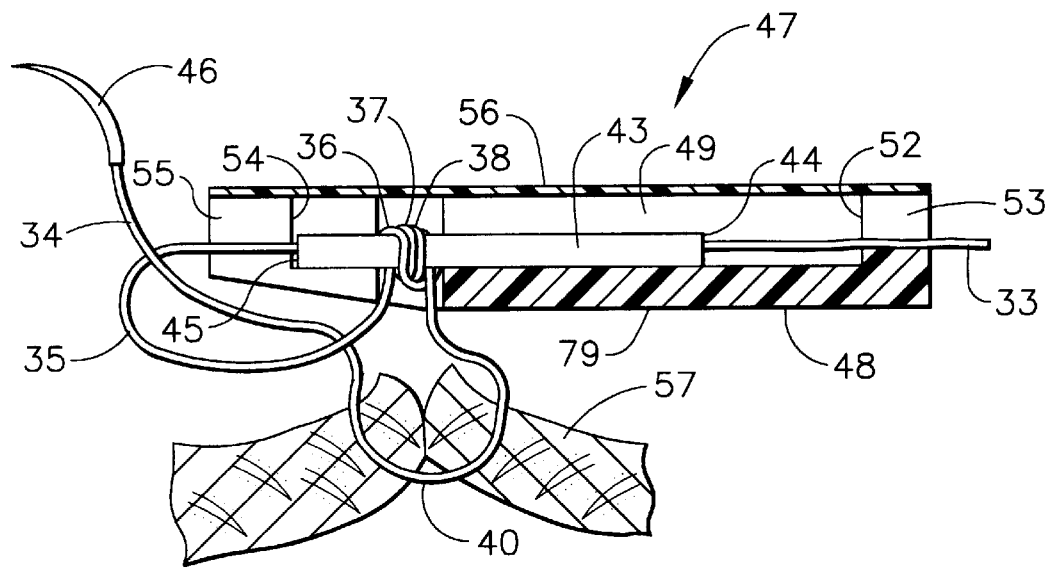
FIGS. 14–15 are section views of the assembly depicted in FIG. 13, including a fragmentary section of tissue, illustrating the use of the partially tied knot to fasten tissue and the steps necessary to form the completed non-slip surgical knot to securely fasten the tissue.
Figure 15:
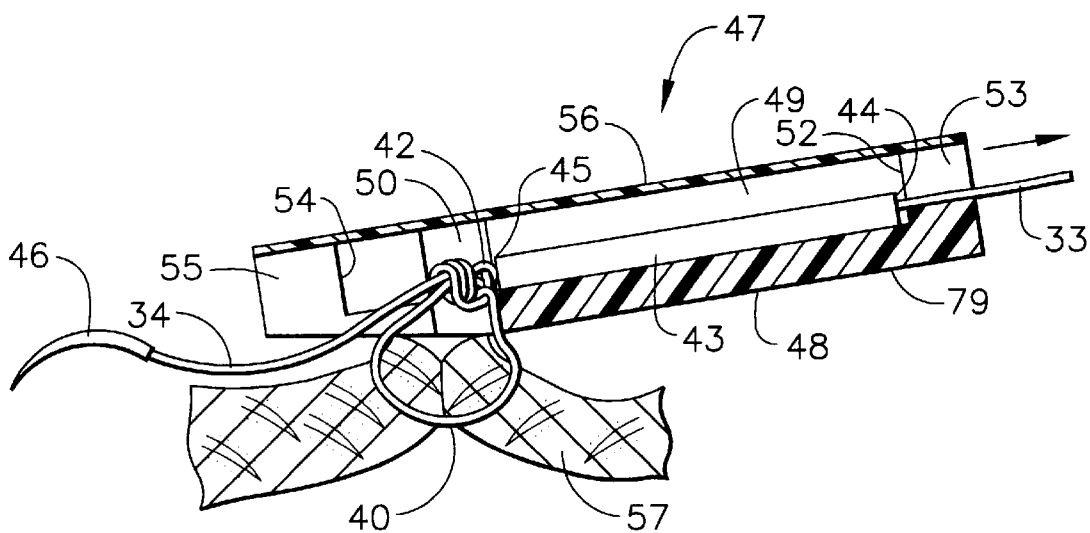

With the core tube fully enclosed within the suture cartridge, the partially tied knot wrapped about the core tube can be deployed to fasten desired bodily tissue as illustrated in FIGS. 14–15. The first step is to position the suture cartridge 47 adjacent bodily tissue 57 desired to be fastened. Next, the surgical needle 46 is passed through the tissue, and into and through the first loop 35 to form the tissue loop 40. The size of the tissue loop is adjusted to provide the appropriate tension on the opposed tissue sections of the bodily tissue 57 desired to be fastened; once the knot is completed to from the non-slip knot, the tissue loop becomes rigidly fixed and further adjustment is unavailable. When the tissue loop 40 is formed and appropriately sized, proximal tension is applied to the proximal length 33 of the suture filament in the direction of the arrow as depicted in FIG. 15. The completed knot is formed when sufficient tension is felt or applied to the proximal length 33.

Advantageously, when tension is applied to the proximal length 33 of the filament, the first loop is pulled and eventually applies a proximal force against the distal end 45 of the core tube 43, causing it to slide proximally as shown in FIG. 15. Since the knot loops abut against the stripping shoulders in the knot recess 50, the knot loops remain stationary even though the core tube slides proximally. When the core tube slides to a position where it is adjacent the proximal edge 52 of the tube slot 49, the knot loops are stripped from the distal end 45 of the core tube. The knot is then fully formed, and the user can remove the cartridge top 56, cut the remaining proximal and distal lengths of suture filament, and remove the core tube. Alternatively, the proximal and distal lengths of suture filament can be exposed without removing cartridge top 56 by releasing the tension on proximal length 33 and pulling the cartridge proximally, thus allowing a portion of the proximal and distal lengths of suture filament contained in the core tube 43 to extend distally from recess 50.

The suture cartridge 47 is advantageous because it is readily adaptable to conventional open and endoscopic instruments, and thus readily facilitates the formation of the knot. The suture cartridge may be disposable, or it can be used on multiple patients. When used on multiple patients, a plurality of disposable core tubes, including the partially tied knot wrapped about the tube, can be loaded serially into the suture cartridge to provide for the placement of numerous surgical knots to fasten tissue using a single suture cartridge.

Figure 21:
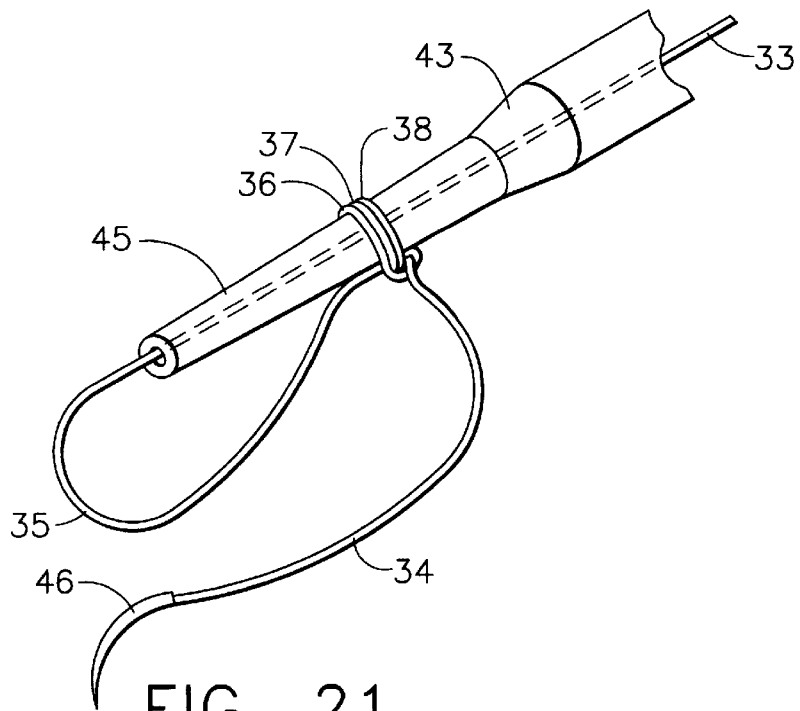
FIGS. 21–23 illustrate the use of the partially tied knot depicted in FIG. 6 formed about a tapered core tube to fasten tissue when the partially tied knot is converted to a completed, non-slip surgical knot.
Figure 22:
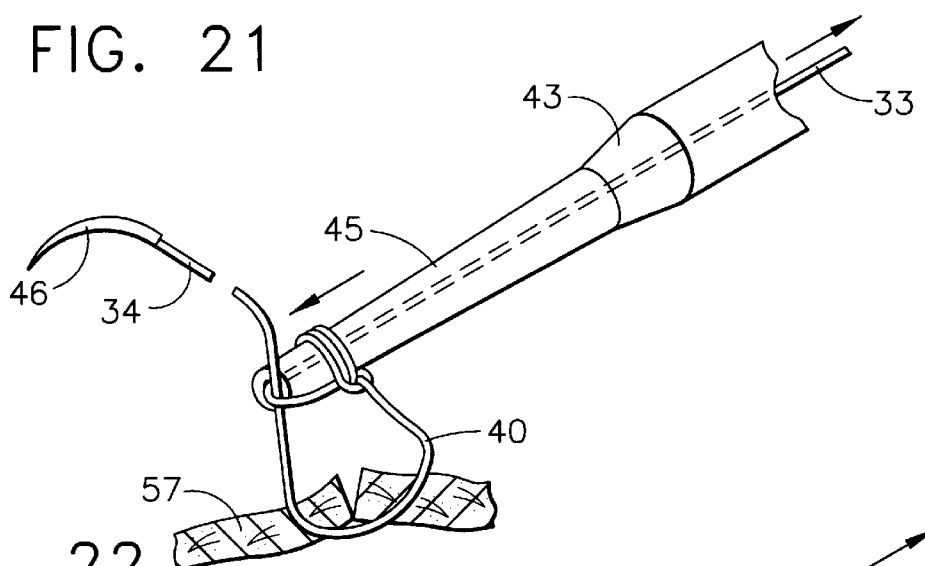
Figure 23:
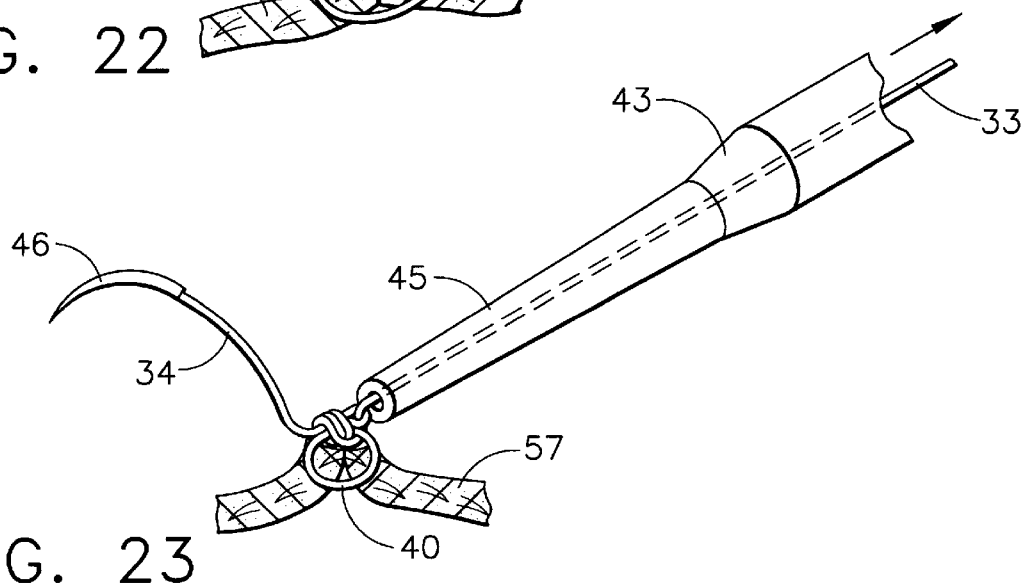

In another example utilizing the core tube concept, the partially tied knot is wrapped about the core tube to facilitate the conversion of the knot to the completed, non-slip knot to fasten tissue. This similar embodiment is illustrated in FIGS. 21–23. The one key difference between what is shown here and that illustrated in FIGS. 9–15 is that the core tube has a tapered distal end. For convenience, the same numbers have been used to identity component parts in FIGS. 21–23 as those used in FIGS. 9–15.

Figure 16:
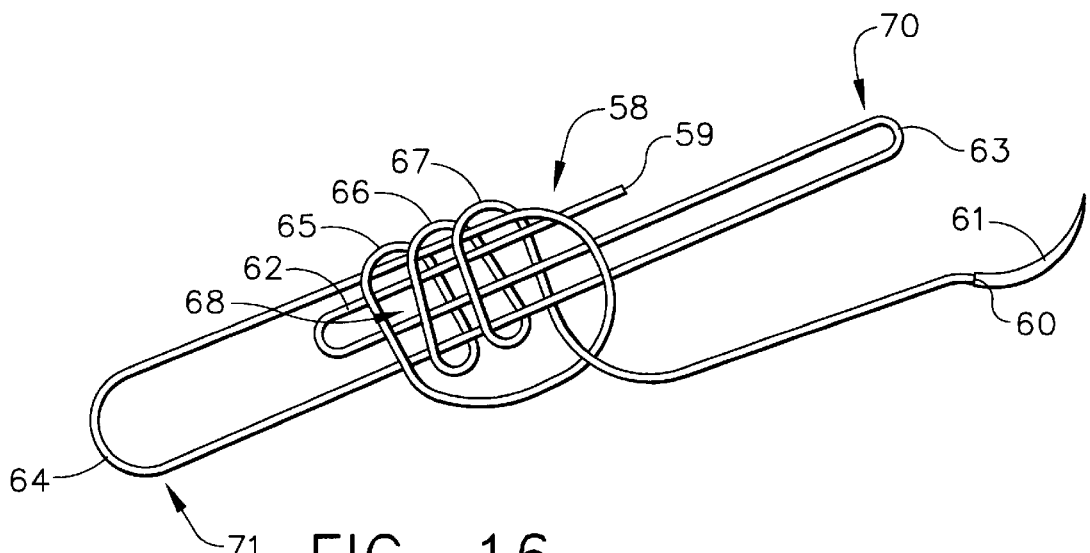
FIGS. 16 and 17 are perspective views depicting the formation of a different partially tied surgical knot from a length of suture filament.
Figure 17:
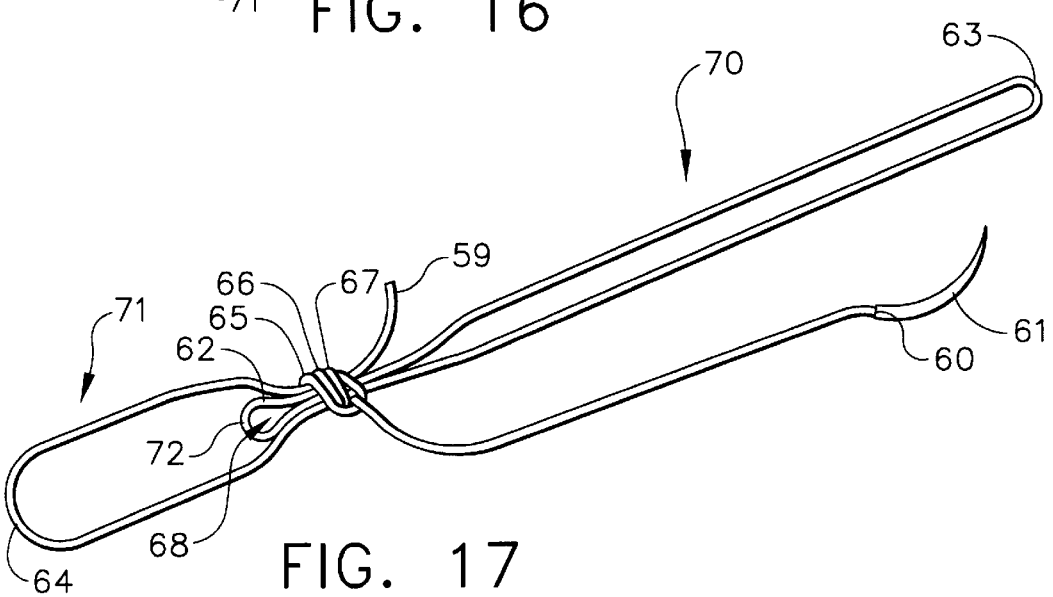

Another example of a partially tied surgical knot is illustrated in FIGS. 16–17. The knot is made from a suture filament 58 which has a proximal end 59 and a distal end 60. A surgical needle 61 is attached to the distal end. The distal end of the filament is manipulated to form the knot while the proximal end of the filament is held stationary. A core loop 62, proximal loop 63 and first loop 64 are initially formed. The proximal loop is at a first end 70 of the knot, and the first loop is at an opposite end 71 of the knot. The core loop is situated between the first and opposite ends of the knot. Knot loops, in the preferred embodiment consisting of second, third and fourth loops, 65, 66, and 67, are formed about the proximal loop 63 and the first loop 64. The knot loops together form a common loop core 68. The core loop is positioned within the common loop core. When tension is applied to the distal end of the surgical filament while the proximal end of the knot loops is supported, the knot loops are tightened. The knot loops are tightened about the first loop, proximal loop and core loop. When tightened, as shown in FIG. 17, the first loop, core loop and proximal loop are securely received in the knot loops, and the partially tied knot is formed.

Referring specifically to FIG. 17, the core loop 62 has a free proximal end 69 extending from the common loop core 68 toward the first end 70 of the knot. The core loop has a loop end 72 which extends from the common loop core in an opposite direction toward the opposite end 71 of the knot. The loop end 72 of the core loop 62 is disposed inside the first loop 64.

The partially tied knot of FIG. 17 can be converted to a completed non-slip knot when axial tension is applied to the proximal loop in the proximal direction while the proximal end of the knot loops is supported. In a manner similar to the deployment of the knot best illustrated in FIGS. 1–8, the knot is converted when the first loop is pulled through the common loop core to form a distal loop. Advantageously, when tension is applied on the proximal loop, not only is the first loop pulled through the common loop core, but also the core loop is pulled through as well. This provides an advantage because the core loop creates a sufficient space represented by the common loop core to enhance the ease of passage of the first loop through the common core to form the completed knot. Easier passage reduces the amount of tension which is need to be applied to the proximal loop to form the completed knot, and therefore increases the degree of control of the user when the knot is being deployed.

Figure 18:
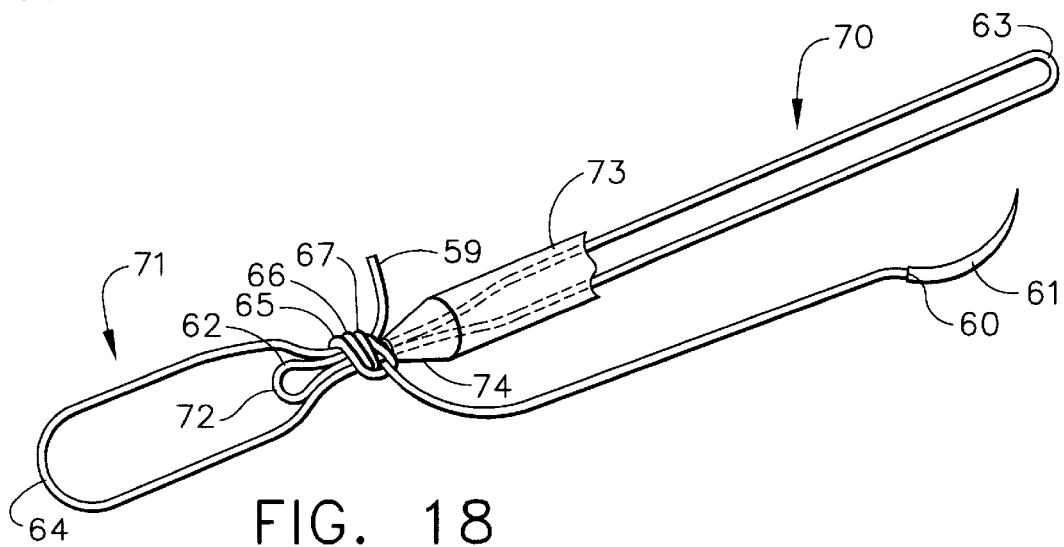
FIG. 18 is a perspective view of the partially tied knot depicted in FIG. 17 formed about a stripping tube.
Figure 19:
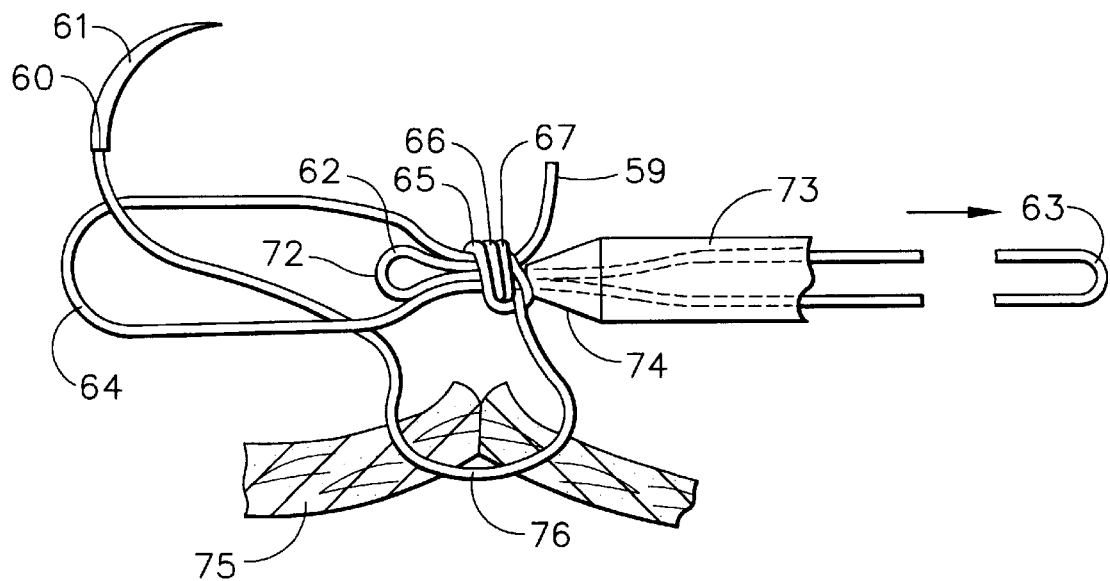
FIGS. 19–20 are side elevation views illustrating the use of the assembly depicted in FIG. 18 to form a completed, non-slip surgical knot to fasten tissue.
Figure 20:
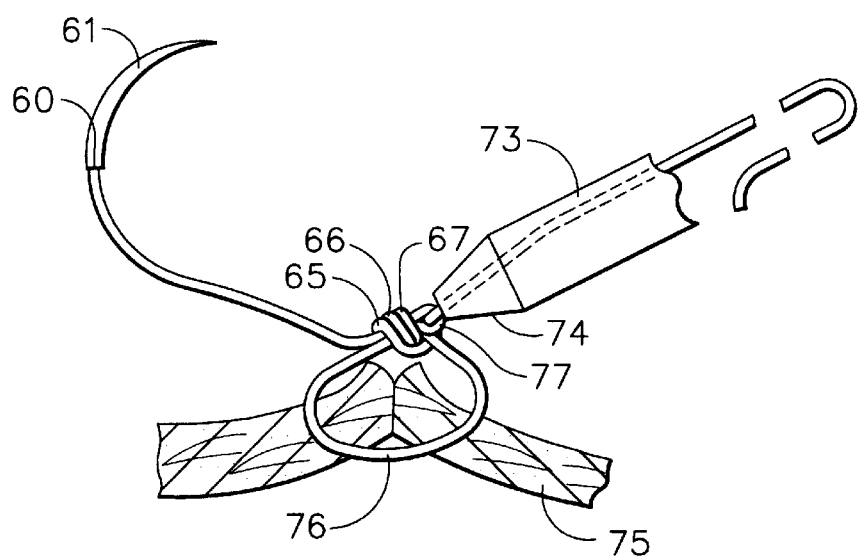

FIGS. 18–20 illustrate the use of the knot depicted in FIG. 17 to fasten tissue, where the knot is deployed in combination with a stripping tube 73. When the partially tied knot of FIG. 17 is formed, the proximal loop 63 is passed through the stripping tube. A portion of the proximal loop extends from a proximal end of the stripping tube. The proximal loop is passed through the stripping tube until the knot loops abut against the distal end of the stripping tube. Significantly, the stripping tube has a tapered distal end 74. The core loop and the first loop extend away from the tapered distal end of the tube. The opening at the distal end of the tube is smaller in diameter than the diameter of the knot loops. Consequently, when tension is applied on the proximal loop in the proximal direction, the knot loops will not pass into the stripping tube.

The conversion of the partially tied knot to the completed knot is performed in a manner substantially similar to that described in connection with the conversion of the previously illustrated knot depicted in FIG. 6.

Referring now to FIGS. 19–20, the stripping tube 73 is positioned adjacent bodily tissue 75 desired to be fastened. The surgical needle 61 is drawn through the tissue. A tissue loop 76 is formed when the surgical needle and distal end of the filament are fed through the first loop 64. Again, it is important to adjust the size of the tissue loop to provide for appropriate tensioning of the fastened tissue before the knot is fully deployed. When the desired tissue loop is formed, tension on the proximal loop 63 is applied in the proximal direction as indicated by the arrow in FIG. 19 to pull the core loop 62 and the first loop 64 through the common loop core. When the first loop emerges from the fourth knot loop 67, the distal loop 77 is formed, and the completed, non-slip knot has been created.

The preferred embodiment of a suture cartridge assembly which can be used in the practice of this invention is detailed in FIGS. 24–39. The preferred embodiment is a further refinement of the assembly illustrated in FIGS. 11–15 which includes the partially tied surgical knot wrapped about a core tube, and subsequently loaded into a suture cartridge.

Figure 24:
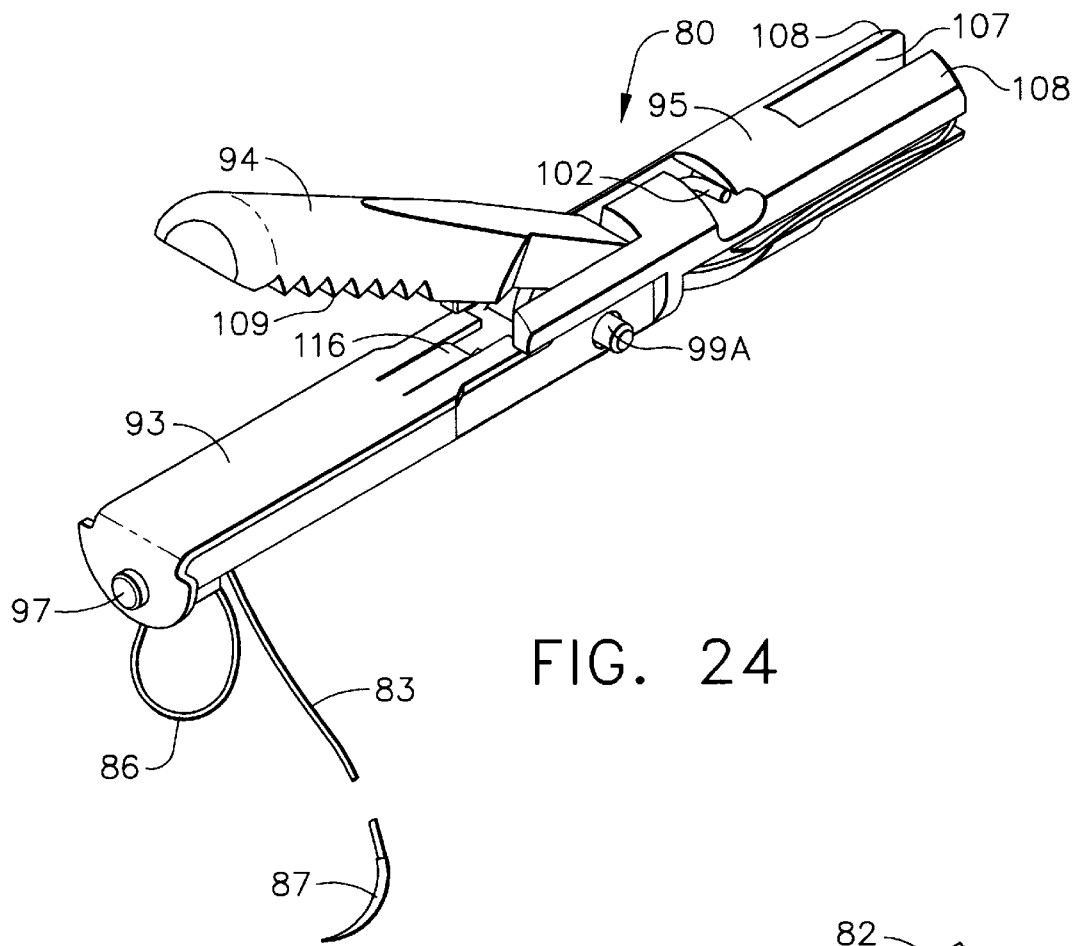
FIG. 24 is a perspective view of a preferred suture cartridge assembly.
Figure 25:
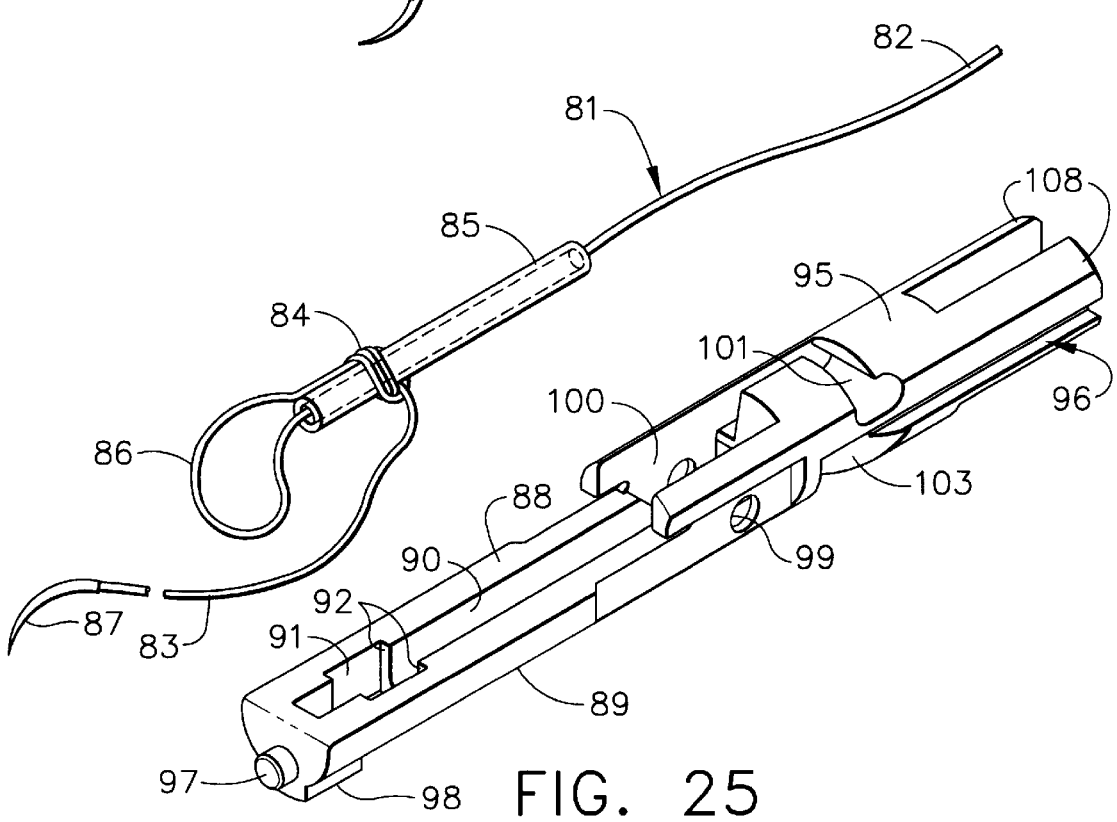
FIG. 25 is an exploded perspective view illustrating the partially tied surgical knot of the preferred suture cartridge assembly wrapped about a core tube and separated from the suture cartridge of the assembly.

Referring initially to FIGS. 24 and 25, the preferred suture cartridge assembly 80 includes a suture filament 81 with proximal and distal ends, 82 and 83, respectively, configured into a partially tied surgical knot 84 wrapped about a core tube 85. The proximal end of the suture filament extends from a proximal end of the core tube, a first loop 86 of the surgical filament extends from a distal end of the core tube, and a surgical needle 87 is attached to the distal end of the surgical filament.

The suture cartridge has top and bottom faces, 88 and 89, respectively, and a slot 90 for receiving the core tube, including the suture filament with its partially tied knot wrapped about the core tube, between the top and bottom faces of the cartridge. The slot contains a knot recess 91 for receiving the partially tied knot of the suture filament, and the partially tied knot abuts a pair of stripping shoulders 92 within the knot recess. When the core tube is loaded into the slot, a portion of the distal end of the suture filament including the surgical needle and the first loop descend from the bottom face of the cartridge. A cartridge top 93 covers the top face of the suture cartridge, and therefore encloses the core tube and a portion of the suture filament.

Importantly, a grasping jaw 94 is pivotally attached to the suture cartridge at a pivot pin 95. The grasping jaw faces the cartridge top and is moveable from an open position spaced from the cartridge top to a closed position adjacent the cartridge top. The grasping jaw is biased in its open position. A cartridge housing 95 which includes a suture filament track 96 is also mounted to the proximal end of the suture cartridge.

Referring now to FIGS. 28–32, the details of the suture cartridge and the cartridge housing integrally mounted to the suture cartridge can be seen. The distal end of the cartridge contains a retaining pin 97 for permanently attaching the cartridge top 93 to the top face of the cartridge. The retaining pin is "heat-staked" to attach the cartridge top to the cartridge. Also included at the distal end of the cartridge is a locating boss 98. There is a pin orifice 99 for receiving the pivot pin for pivotally attaching the grasping jaw to the cartridge. The pivot pin received through the orifice also serves to fix the cartridge housing to the suture cartridge. A central aperture 100 is contained at the distal end of the cartridge housing to provide an opening for receiving the proximal end of the grasping jaw. Also contained within the cartridge housing is a torsion spring slot 101 for receiving a torsion spring 102 (see FIGS. 24 and 33) to bias the grasping jaw in its open position. The torsion spring has an upper arm 113, a torsion loop 114 and a jaw arm 115.

The suture filament track 96 of the cartridge housing includes a ventral channel 103 which merges into a left side suture groove 104 extending proximally to the proximal end of the cartridge housing. At the proximal end of the cartridge housing, a pair of lateral filament slots 105 are displayed. Continuing from the lateral filament slots, a right side suture groove 106 is embedded within the cartridge housing. The cartridge housing also contains a hook slot 107 surrounded by a pair of spaced-apart hook tines 108.

Figure 34:
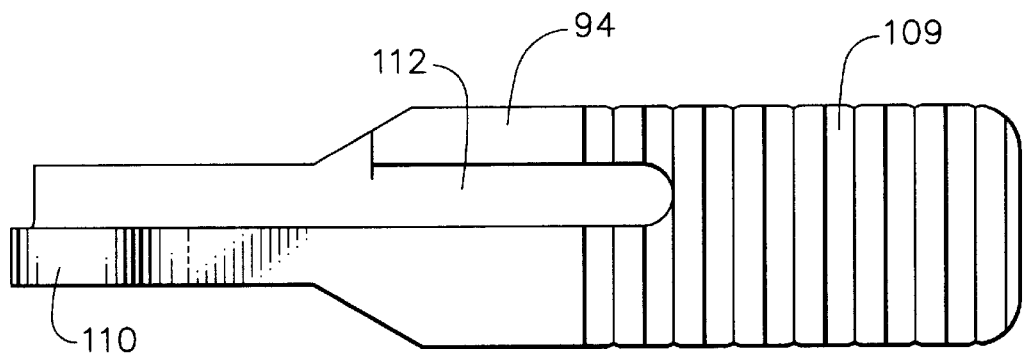
FIG. 34 is a bottom view of the grasping jaw of the cartridge assembly of FIG. 24.
Figure 35:
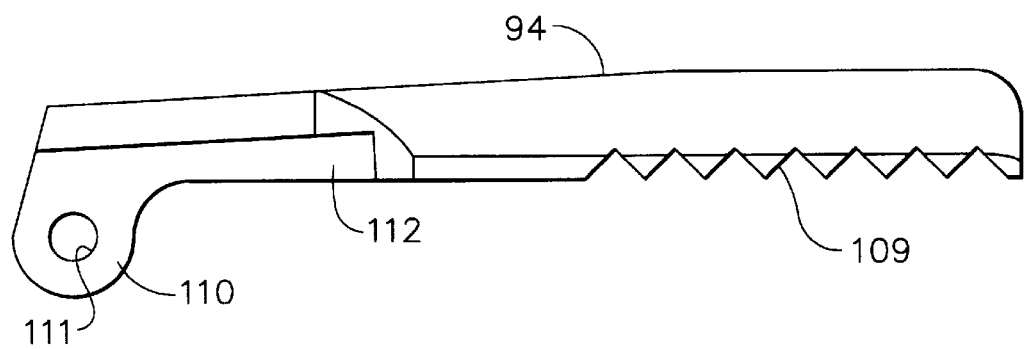
FIG. 35 is a right side elevation view of the jaw of FIG. 34.
Figure 36:
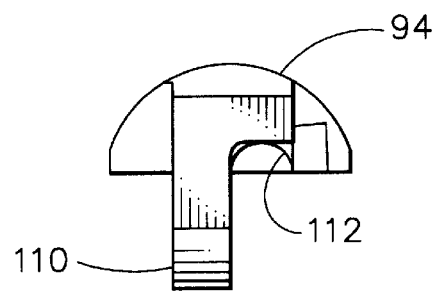
FIG. 36 is a proximal end elevation view of the jaw taken along line 36—36 of FIG. 35.

Referring now to FIGS. 34–36, the details of the grasping jaw 94 can be seen. The grasping jaw has an inner serrated surface 109 to facilitate the grasping of tissue, suture filament or the surgical needle. It contains a jaw lug 110 including a jaw orifice 111 for receiving the pivot pin 95 for its pivotal mount relative to the suture cartridge. It also includes a spring arm slot 112 for receiving the torsion spring 102. The proximal end of the cartridge top has a spring tab 116. The spring tab biases and maintains core tube 85 distally during assembly and knot deployment.

In the preferred embodiment, the suture cartridge assembly is a disposable assembly intended to be discarded after a single patient use. The suture cartridge and the housing are preferably composed of a biocompatible, injection-molded plastic, and the grasping jaw is preferably made from medical grade stainless steel. Alternatively, the suture cartridge assembly could be fabricated from a suitable metal in a metal injection molding (MIM) process, which is a conventional forming technique adaptable for fabricating conventional staple cartridges for surgical staplers and cutters.

Figure 26:
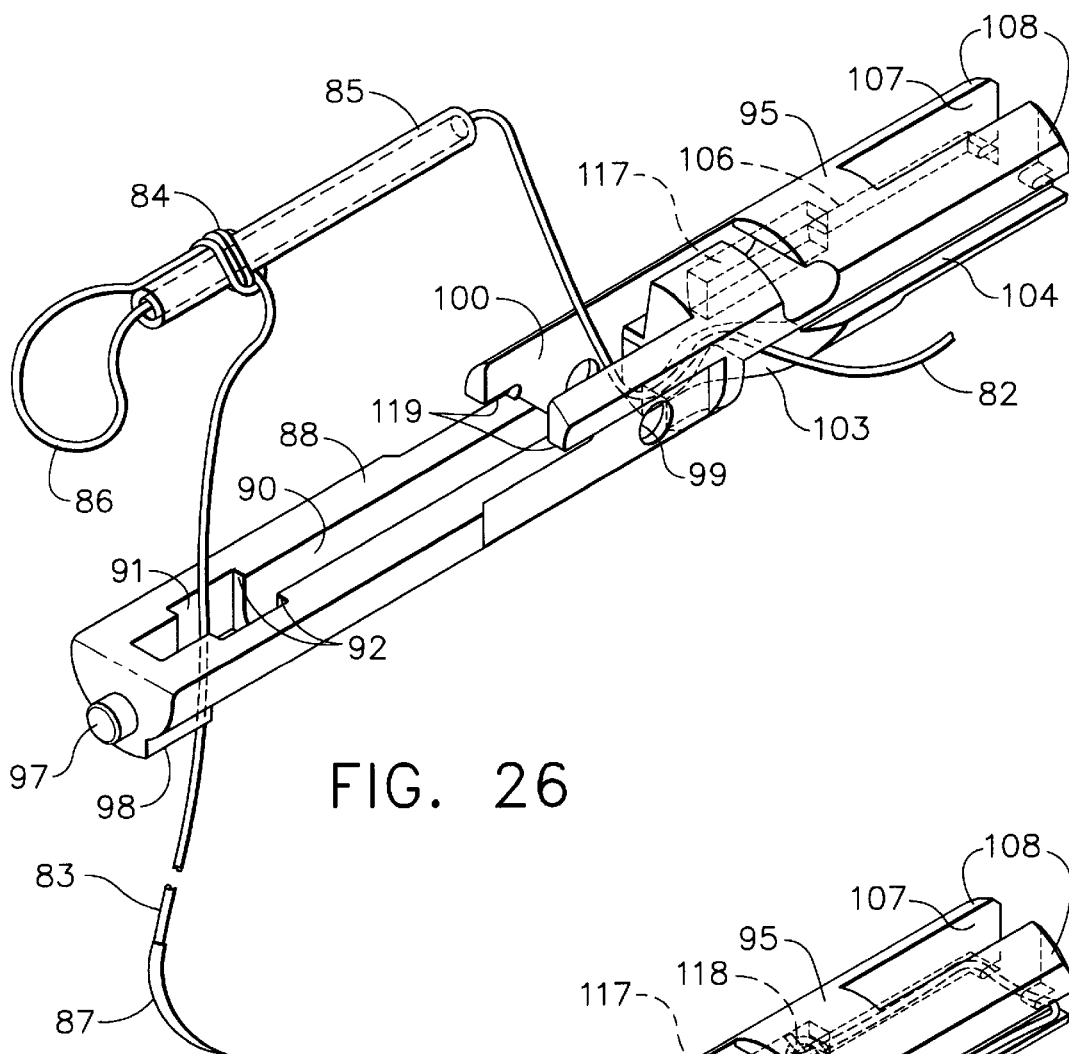
FIG. 26 is an exploded perspective view illustrating the initial step of assembling the suture cartridge assembly of FIGS. 24 and 25 where the surgical needle attached to the distal end of the suture filament is loaded into the cartridge slot of the suture cartridge.
Figure 27:
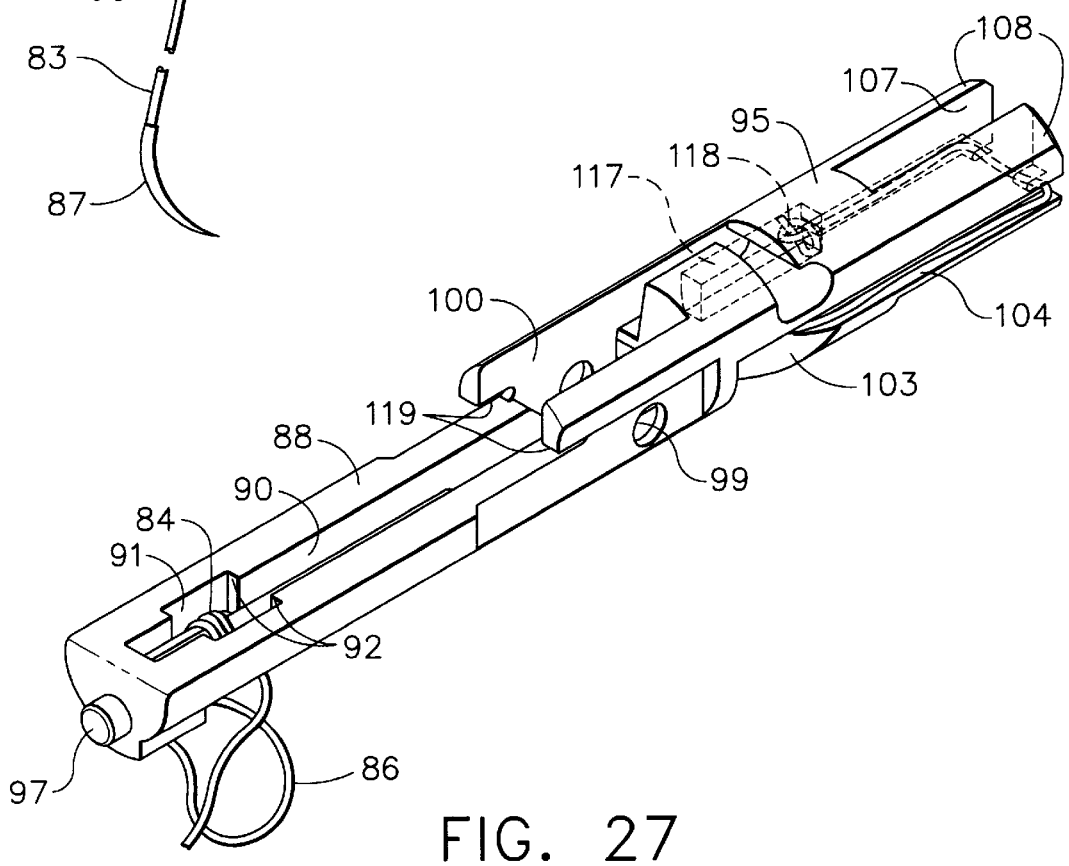
FIG. 27 is a perspective view illustrating a further step of assembly following the loading of the core tube into the cartridge slot, where the proximal end of the suture filament is secured to a cartridge housing attached to the suture cartridge.
Figure 28:
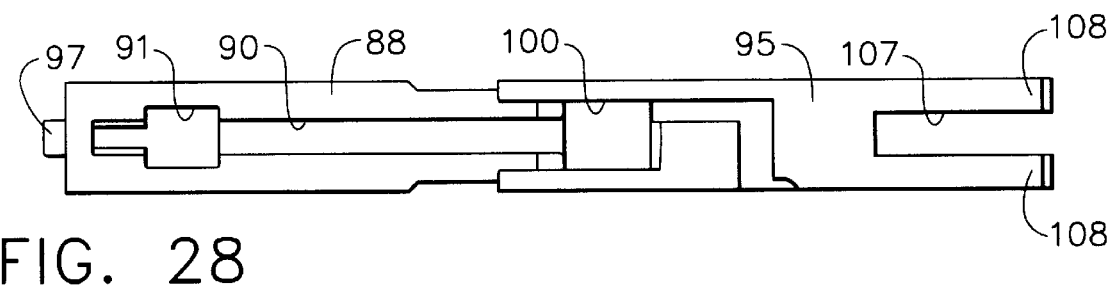
FIG. 28 is a plan view of the suture cartridge of the preferred suture cartridge assembly of FIG. 24 including the cartridge housing.
Figure 29:
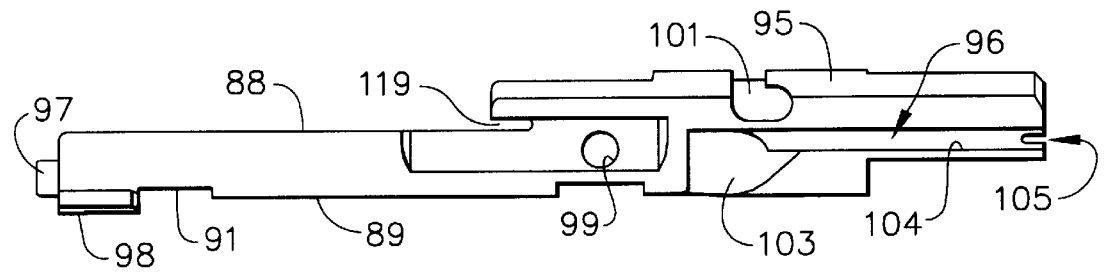
FIG. 29 is a left side elevation view of the cartridge of FIG. 28.
Figure 30:
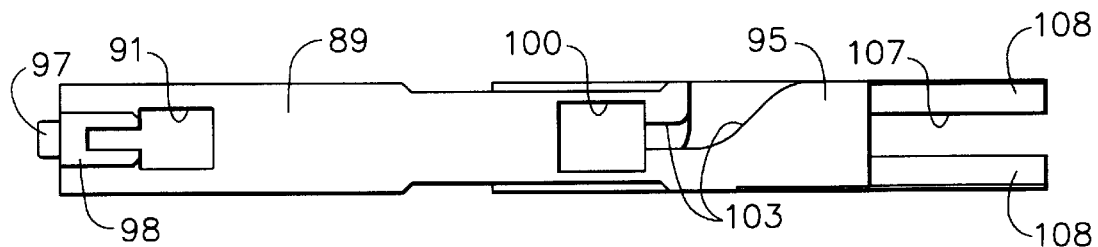
FIG. 30 is a bottom view of the cartridge of FIG. 28.
Figure 31:
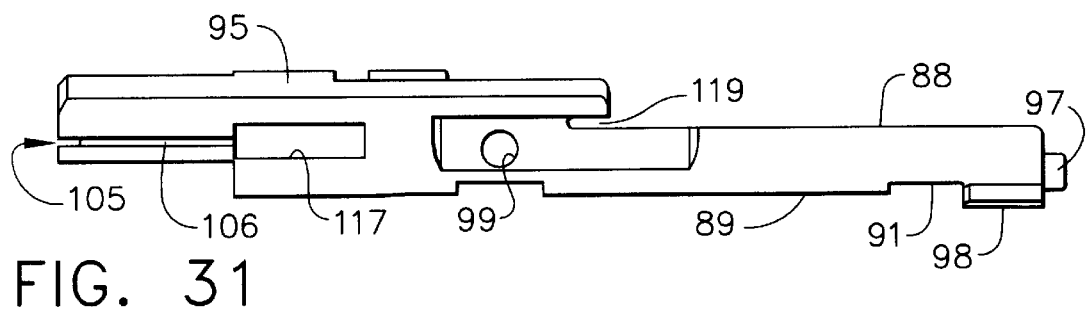
FIG. 31 is a right side elevation view of the cartridge of FIG. 28.
Figure 32:
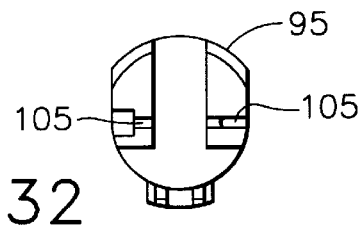
FIG. 32 is a rear or proximal end elevation view of the cartridge of FIG. 28.

FIGS. 26 and 27 illustrate how the core tube is mounted into the suture cartridge, and how the proximal end of the suture filament is wrapped about the periphery of the cartridge housing within the suture filament track. As the core tube is mounted into the slot in the cartridge, the surgical needle and a portion of the distal end of the suture filament are passed through the slot, and the partially tied surgical knot is positioned into the knot recess where the knot abuts against the stripping shoulders and the first loop descends from the bottom face of the cartridge. The proximal end of the suture filament is passed through the ventral channel of the cartridge housing and is wrapped about the left side suture groove, lateral suture slots and right side suture groove of the suture filament track before emerging at an anchor recess 117 within the cartridge housing. A knot anchor 118 is tied at the proximal end of the suture filament within the anchor recess to place the suture filament in a fixed position within the cartridge housing. Also worthy of note in observing FIGS. 26 and 27 are the pair of retaining slots 119 at a junction between the cartridge housing and the top face 88 of the suture cartridge for further retaining the cartridge 93 top when it is mounted onto the top face of the suture cartridge.

Figure 33:
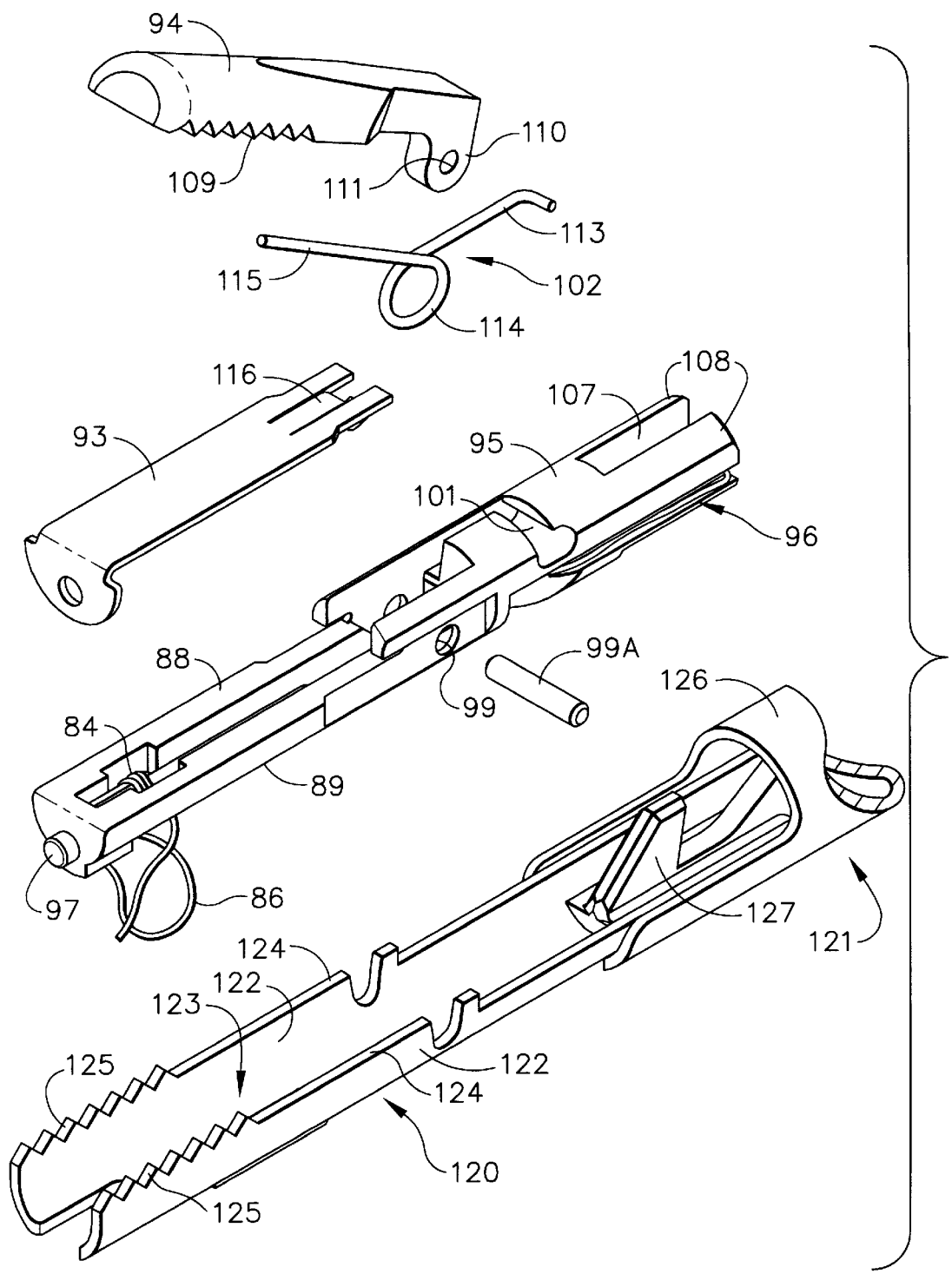
FIG. 33 is an exploded perspective view illustrating the placement of the loaded suture cartridge assembly of FIG. 24 into a cartridge carrier.

In an especially preferred embodiment, the loaded suture cartridge assembly which can be used in the practice of this invention is received within a cartridge carrier 120 of a surgical instrument 121 to further facilitate the deployment of the knot and the grasping of tissue, the surgical needle or the filament. Referring specifically to FIG. 33, the suture cartridge including the cartridge housing is loaded into and received within the cartridge carrier. The cartridge carrier has a pair of containing walls 122 defining a channel 123 for receiving the cartridge assembly. Each containing wall has a top edge surface 124, and a serrated edge surface 125 at its distal end. The surgical instrument which includes the cartridge carrier for receiving the suture cartridge advantageously includes a reciprocating closure tube 126 for urging the jaw to its closed position when the closure tube is reciprocated forwardly, and to its open position when the closure tube is reciprocated rearwardly. Such an instrument preferably includes a hook 127 which is received in the hook slot 107 between the pair of hook tines 108 in the cartridge housing. When the hook is retracted, it pulls the proximal end of the suture filament within the suture filament track 96 of the suture cartridge housing, and the knot is deployed in a manner substantially similar to that illustrated in FIGS. 11–15.

Figure 37:
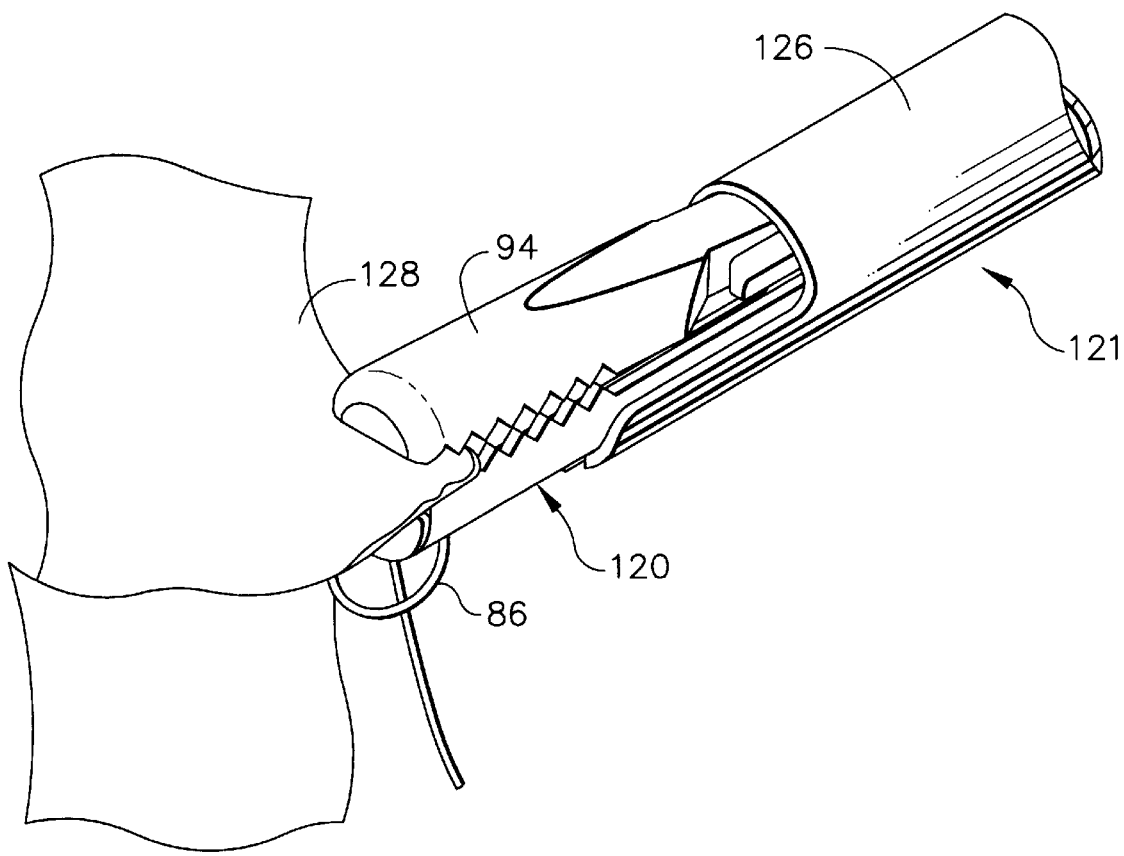
FIG. 37 is a perspective view of the cartridge assembly of FIG. 24 mounted in a cartridge carrier and used in cooperation with a closure tube of a surgical instrument to grip tissue.
Figure 38:
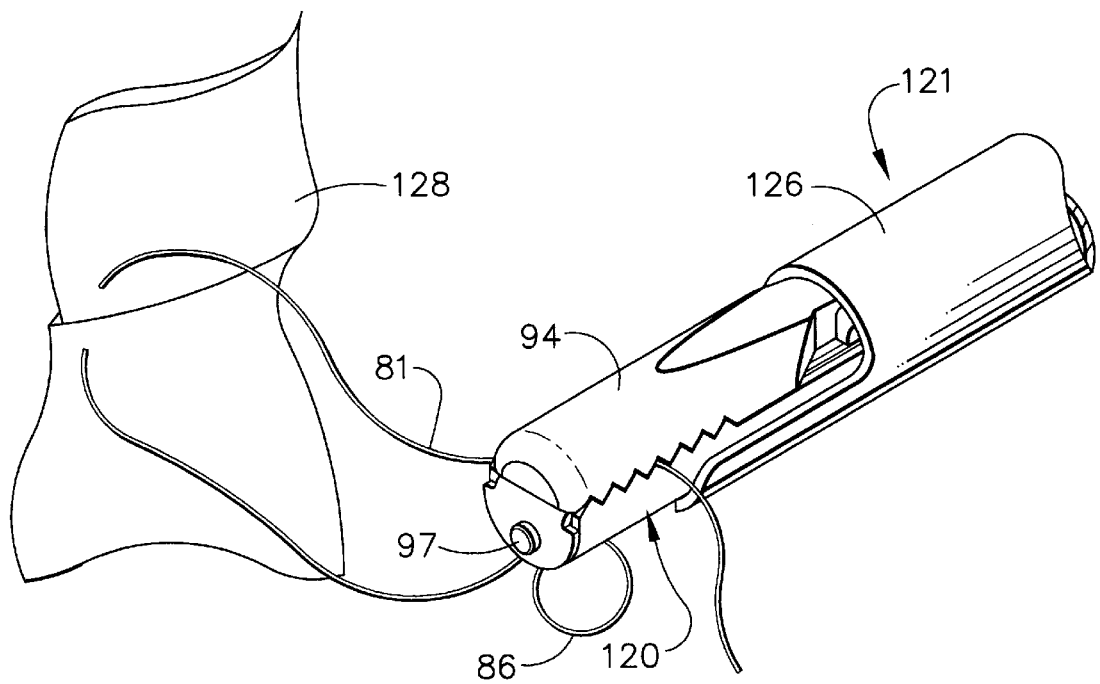
FIG. 38 is a perspective view similar to that of FIG. 37 where the cartridge assembly is used to grip a segment of the suture filament.
Figure 39:
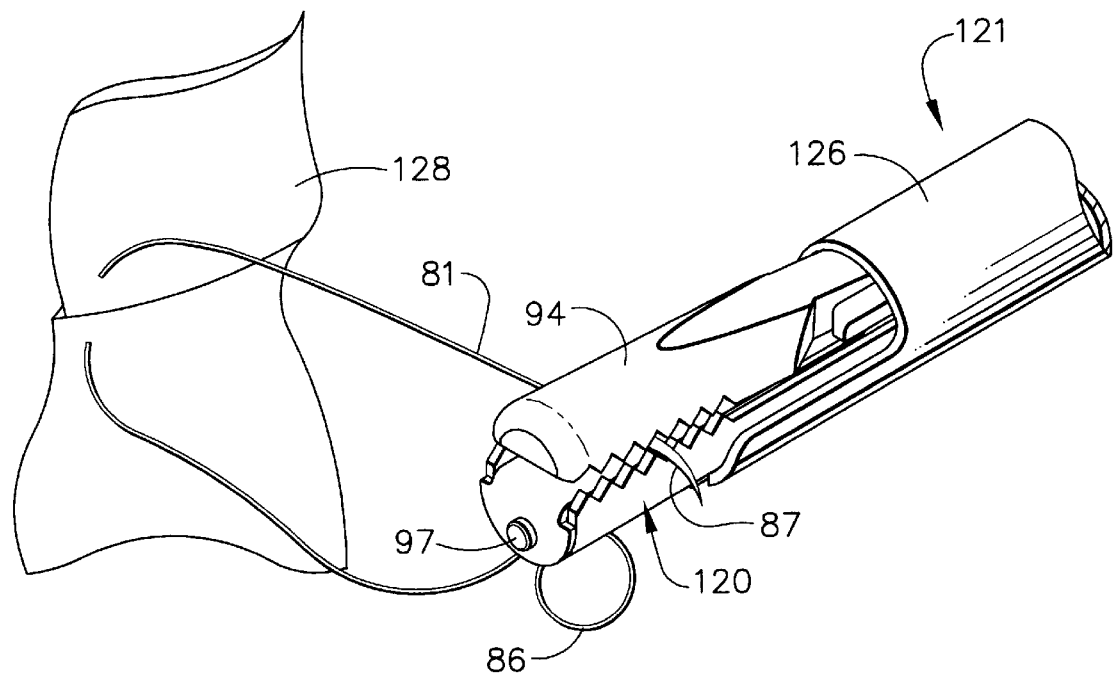
FIG. 39 is a perspective view similar to that of FIG. 37 where the cartridge assembly is used to grip a surgical needle.

Referring now to FIGS. 37–39, it can be observed that when the cartridge assembly is loaded into the carrier, the serrated edge surfaces of the containing walls of the cartridge carrier protrude from the cartridge top of the suture cartridge, and mesh with the inner serrated surface of the grasping jaw when the grasping jaw is in its closed position. In so doing, the meshing surfaces facilitate the grasping of tissue 128 (FIG. 37), the surgical filament 81 (FIG. 38) and the surgical needle 87 (FIG. 39). The suture cartridge assembly of this invention therefore facilitates not only the deployment of a fully formed knot from a partially formed knot, but also the manipulation of tissue or the suture filament including the surgical needle which is so important during the surgical procedure to easily place the knot.

The load assist device which can be used cooperatively with the preferred surgical instrument of this invention, and the manner in which a cartridge carrier on the surgical instrument can be loaded with a suture cartridge contained in the load assist device, are illustrated in FIGS. 40–49.

Figure 42:
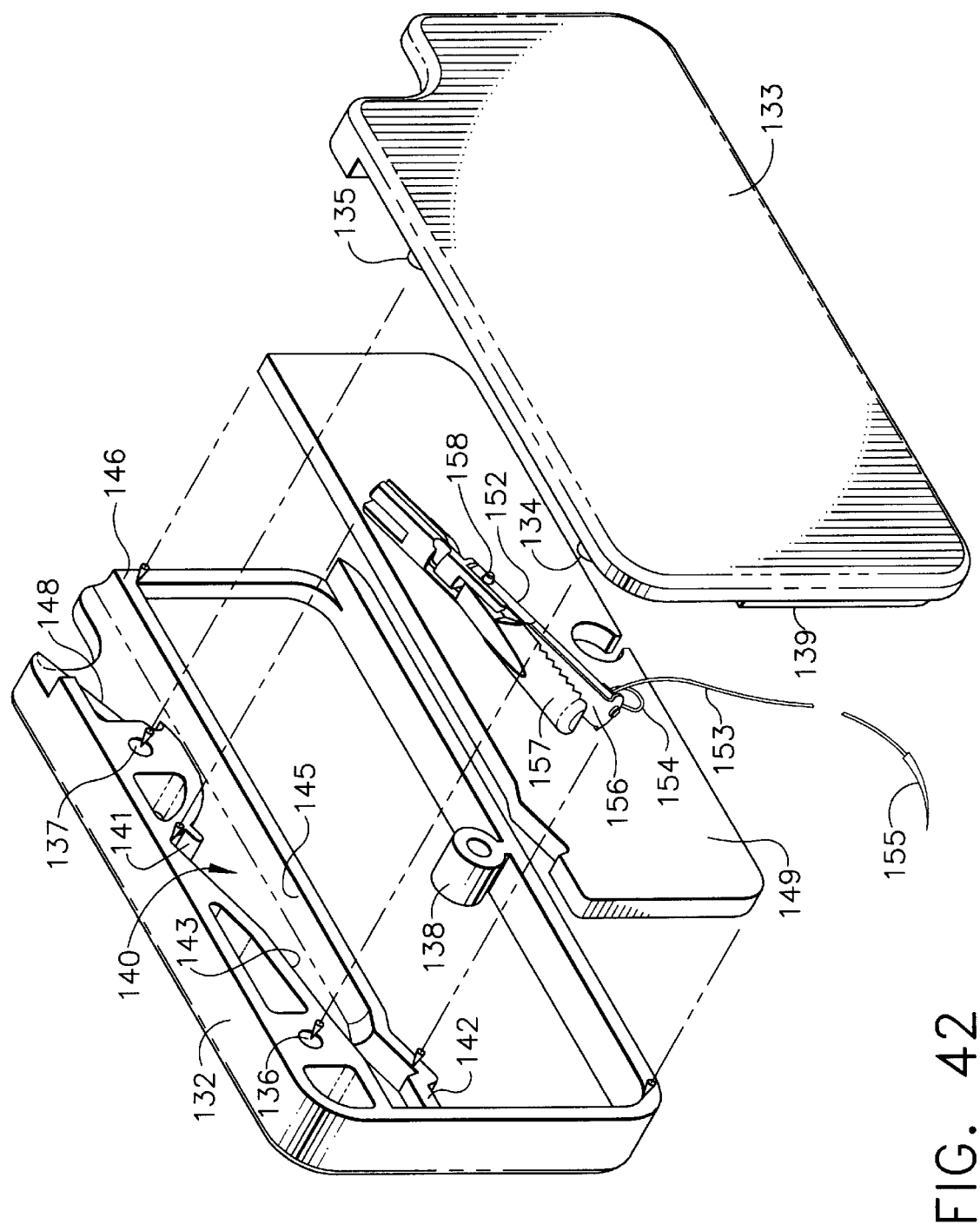
FIG. 42 is an exploded view of the load assist device of FIG. 40 illustrating the enclosure of the suture cartridge in the cartridge casing.

Referring initially to FIGS. 40–42, the details of the load assist device can be seen. The load assist device 130 has a rigid and transparent cartridge casing 131, for ease of handling and to readily observe the contents within the casing when the cartridge carrier of the surgical instrument is loaded with the suture cartridge and removed from the transparent casing. The casing consists of a base 132 and a top cover 133 facing the base. The top cover is releasably attached to the base. The cover has distal and proximal pins, 134 and 135, respectively, which are received in corresponding distal and proximal bosses, 136 and 137, on the base of the casing. To further secure the top cover to the base, a lower boss 138 on the base receives a corresponding lower pin (not shown) extending from the top cover, and a casing support rib 139 also extends from the top cover and frictionally engages the base.

The cavity between the base and the top cover of the cartridge casing defines a cartridge storage space 140. The cartridge storage space includes a proximal retainer 141, a distal retainer 142 spaced from the proximal retainer, and a jaw retaining ledge 143 between the proximal and distal retainers. The cartridge storage space receives and secures the suture cartridge within the cartridge casing of the load assist device.

The base and top cover of the cartridge casing also define a carrier aperture 144 for enabling the insertion and withdrawal of a cartridge carrier of a surgical instrument for deploying a knot during a surgical procedure from the suture filament contained in the cartridge. An interior carrier channel 145 provides a passageway between the carrier aperture and the cartridge storage space so that when the cartridge carrier of the instrument is inserted through the aperture, it can pass through the channel until it enters the cartridge storage space for the loading of the cartridge onto the carrier. The channel is bounded by a base support ledge 146 extending from the base, and a cover support rib 147 extending from the top cover in a mutually opposed relationship to the base support ledge. A sloped inlet ramp 148 is also provided to further facilitate the insertion and withdrawal of the cartridge carrier of the instrument. The sloped inlet ramp extends from the carrier aperture to the carrier channel.

The base 132 of the cartridge casing contains a pad 149 upon which the suture filament of the suture cartridge is placed. The top cover has a suture retainer 150 for retaining the suture filament of the suture cartridge in a fixed position on the pad when the top cover is secured onto the base. In a similar fashion, the top cover has a needle retainer 151 for retaining the surgical needle attached to the suture filament of the suture cartridge on the pad when the top cover is placed on the base of the cartridge casing.

The cartridge storage space 140 within the cartridge casing of load assist device receives a suture cartridge 152. The suture cartridge contains a surgical filament 153 configured into a partially tied knot with a first loop 154, and a surgical needle 155 attached to a distal end of the surgical filament. The suture cartridge has a cartridge top 156, and a jaw 157 facing the cartridge top. The jaw is pivotally movable at a pivot pin 158 from an open position spaced from the cartridge top to a closed position adjacent the cartridge top. The jaw is normally biased in its open position.

The first loop 154 and the surgical filament 153 are held within the assembly as depicted in FIG. 42 on the central plane offset midway between the external faces of the base 132 and cover 133. So constrained, the loop 154 and filament 153 do not become tangled or pinched during the loading of the suture cartridge 152 into the cartridge carrier.

The preferred suture cartridge in the practice of this invention is the assembly depicted in FIGS. 24–39. The suture cartridge 152 is situated in the cartridge storage space so that a proximal end of the suture cartridge sits on the proximal retainer 141. A distal end of the suture cartridge sits on the distal retainer 142, and the jaw 157 is retained against the jaw retaining ledge 143. In order to firmly secure the suture cartridge in the cartridge storage space, the spacing between the distal retainer and the jaw retaining ledge is such that the jaw is oriented in a position between its open and closed positions. In this manner, the biasing action of the jaw against the jaw retaining ledge helps to firmly plant the suture cartridge within the cartridge storage space. It is also noteworthy that the suture cartridge within the cartridge storage space is sloped downwardly from the cartridge proximal end to the cartridge distal end. The assembly depicted in FIG. 42 may be packaged and sterilized using conventional techniques such as gamma irradiation or ethylene oxide exposure.

A surgical instrument 159 of this invention can be used in cooperation with the load assist device for loading the suture cartridge from the cartridge casing onto the instrument for subsequent deployment of a knot from the suture filament contained in the suture cartridge. The surgical instrument can be a conventional open instrument or an endoscopic instrument adapted for minimally invasive surgery. Preferably, the instrument is an endoscopic surgical instrument. Advantageously, it has a cartridge carrier 160 configured for insertion and withdrawal into and out of the carrier aperture of the cartridge casing, and passage through the carrier channel to the cartridge storage space. Of course, it must also be configured to receive the suture cartridge from the cartridge storage space. Preferably, the surgical instrument has a closure tube 161 movable from a retracted position to an extended position for opening and closing the jaw relative to the cartridge top of the suture cartridge.

Referring now to FIGS. 43–49, there is shown the sequence of steps for loading the cartridge carrier of the surgical instrument with the suture cartridge encased in the cartridge storage space of the cartridge casing of the load assist device. In FIG. 43, the cartridge carrier is oriented for insertion into the carrier aperture and passage through the carrier channel. In FIG. 44, the cartridge carrier has been inserted into the carrier aperture, and is passed through the carrier channel in a loading direction indicated by the arrow until it has made contact with the suture cartridge within the cartridge storage space of the cartridge casing. As a result of the sloped orientation of the suture cartridge, the cartridge carrier contacts the suture cartridge at a point intermediate between the proximal and distal ends of the suture cartridge. Referring now to FIG. 45, the carrier is moved distally in the cartridge storage space, causing the suture cartridge to be dislodged from the distal and proximal retainers in the cartridge storage space. The dislodgment of the suture cartridge from the distal and proximal retainers, in combination with the movement of the cartridge carrier distally within the cartridge storage space, causes the suture cartridge to be received in the cartridge carrier of the instrument. As the suture cartridge is loaded into the cartridge carrier when the cartridge carrier is moved distally, the closure tube of the surgical instrument is maintained in its retracted position. It is also noteworthy that because of the slight pressure exerted on the suture filament and surgical needle sitting on the pad from the suture and needle retainers of the top cover, there is no interfering movement of the suture filament and needle during loading operation. In FIG. 46, once the cartridge carrier of the instrument is loaded with the suture cartridge, the closure tube of the instrument is moved from its retracted position to its forward position, thus securing the suture cartridge in the cartridge carrier of the instrument.

Figure 49:
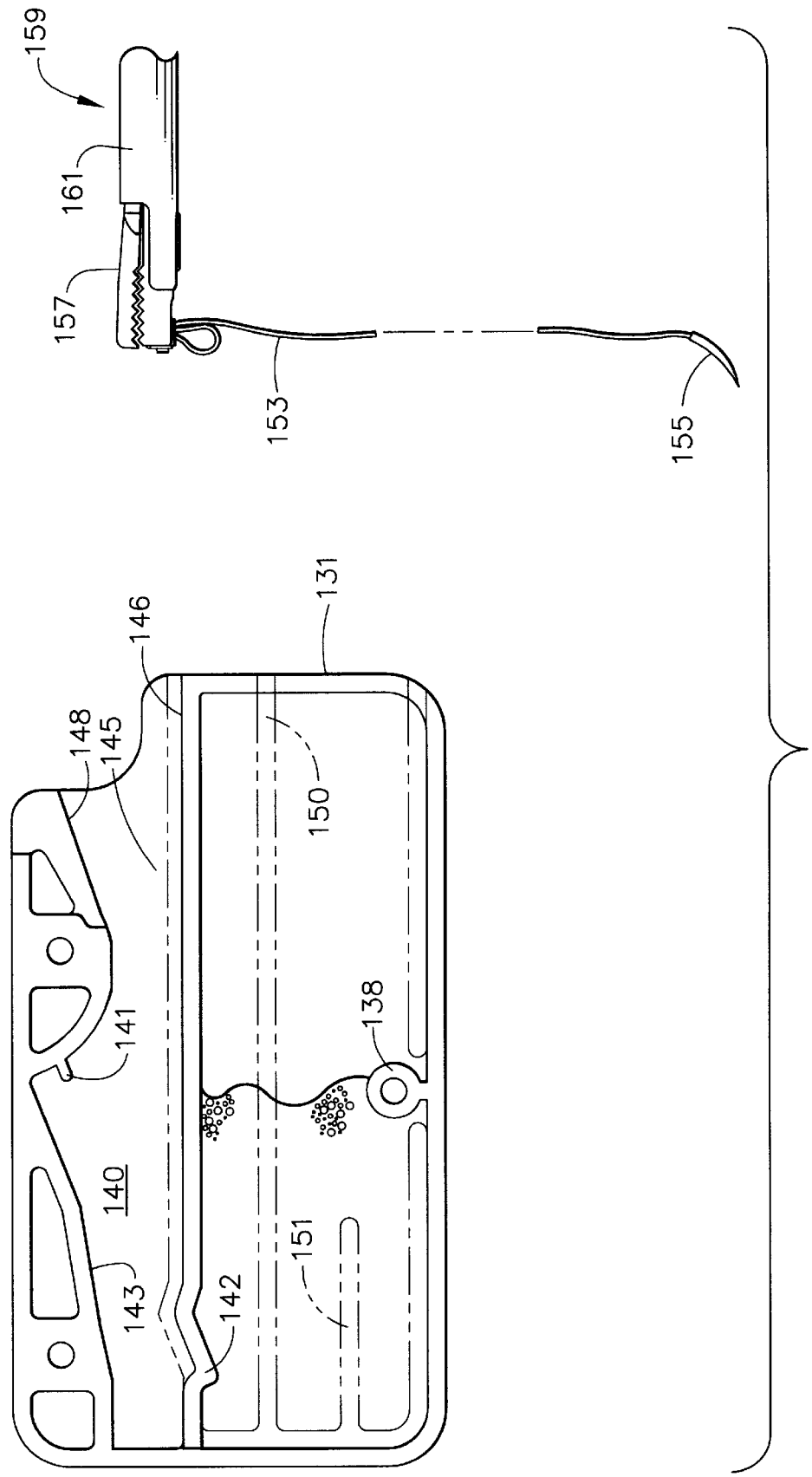
FIG. 49 is a view in side elevation of the interior of the load assist device of FIG. 40 illustrating the separation of the loaded cartridge carrier.

Observing specifically FIGS. 47–49, the loaded cartridge carrier of the instrument is removed from the cartridge casing of the load assist device. It is removed simply by withdrawing the cartridge carrier from the cartridge storage space, carrier channel and carrier aperture of the cartridge casing in an unloading direction as indicated by the arrow in FIG. 47.

Advantageously, there is a small gap between the base ledge 146 and cover support rib 147 bounding the interior carrier channel within the cartridge casing so that the suture filament and surgical needle can freely pass out of the cartridge casing (See FIG. 41 to see the gap). Likewise, the pressure which the suture and needle retainers exert on the suture filament and needle sitting on the pad within the base of the cartridge casing is minimal so that the filament and needle can readily pass out of the cartridge casing.

Once the surgical instrument is used to deploy a knot from the suture filament contained in the surgical cartridge which has been loaded into the cartridge carrier of the instrument, the surgeon or operating room assistant can unload the spent cartridge and dispose of it. If additional surgical knots need to be deployed, the surgeon or operating room assistant need only procure another load assist device of this invention to facilitate the loading of a second suture cartridge onto the cartridge carrier of the instrument.

FIGS. 50–60 show a surgical instrument 121 which is the preferred embodiment of this invention. Referring first to FIG. 51, the handle assembly 300 of the surgical instrument includes a grip 192 having a proximal end 193 and a distal end 194, a trigger 180, a lever 220, a left and a right release button 240 and 238 respectively, one on each side of the grip 192 (see FIG. 50), and a trigger latch 281. The closure tube 126 is attached to the proximal end of the grip, and is constrained to slide longitudinally within the grip as controlled by the actuation of the trigger 180. This function allows the loading and unloading of the suture cartridge assembly 80 (see FIG. 24) according to the steps depicted in FIGS. 43–49 and the opening and closing of the jaw 94 as depicted in FIGS. 37–39. The actuation of the lever 220 causes the deployment of the partially tied knot by pulling axially the proximal filament 33 of the suture thread as depicted in FIGS. 15, 19, and 23, resulting in a completed knot as shown in FIG. 8. The left and right release buttons 240 and 238, allow upon simultaneous actuation, the opening of the trigger 180 in order to load and unload the suture cartridge assembly. The trigger latch 281 holds the trigger against the grip after the full actuation of the trigger, and releases the trigger from the grip after the subsequent, full actuation of the trigger.

Figure 53:
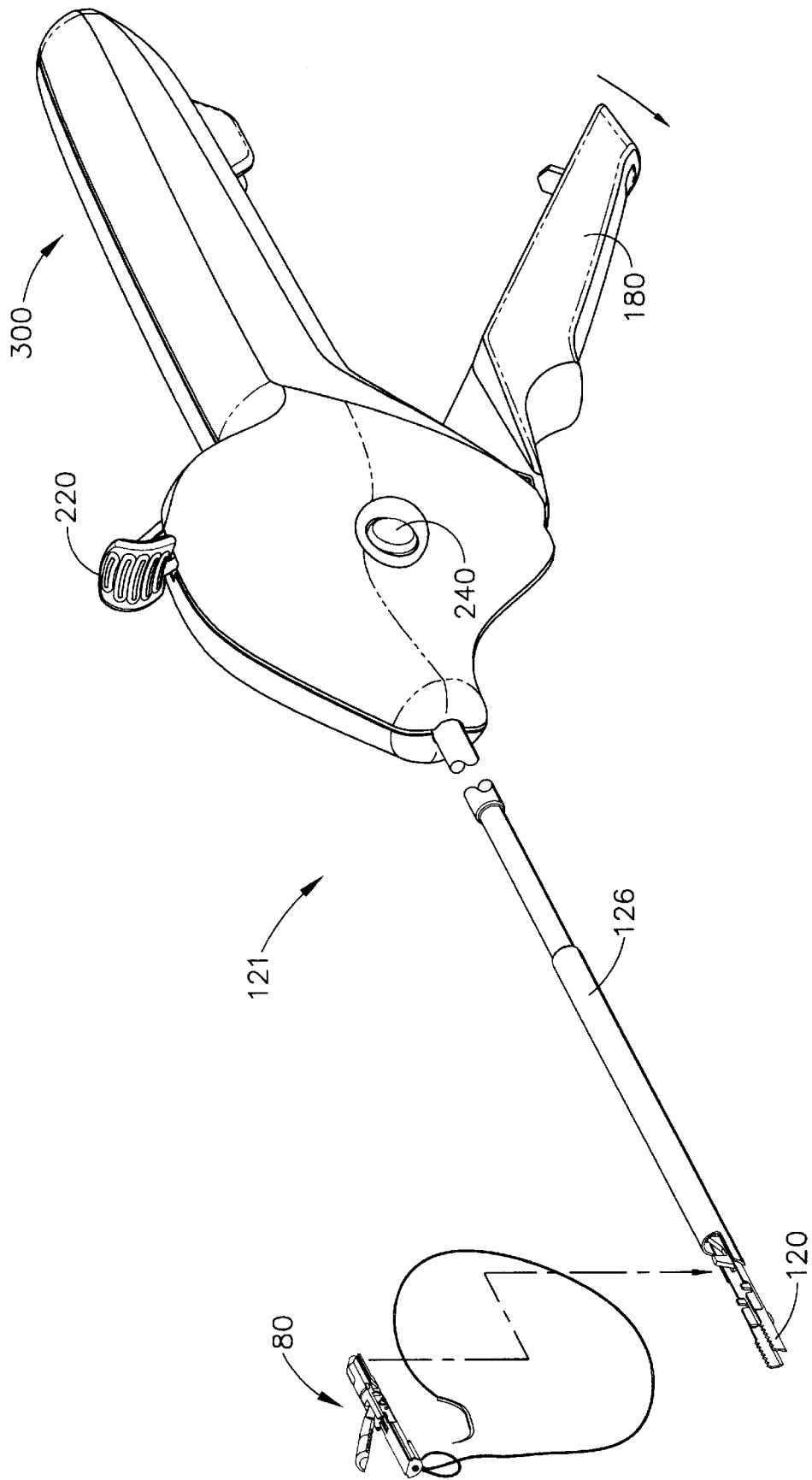
FIG. 53 is a perspective view of the surgical instrument of FIG. 51 in the configuration for receiving a suture cartridge assembly.
Figure 54:
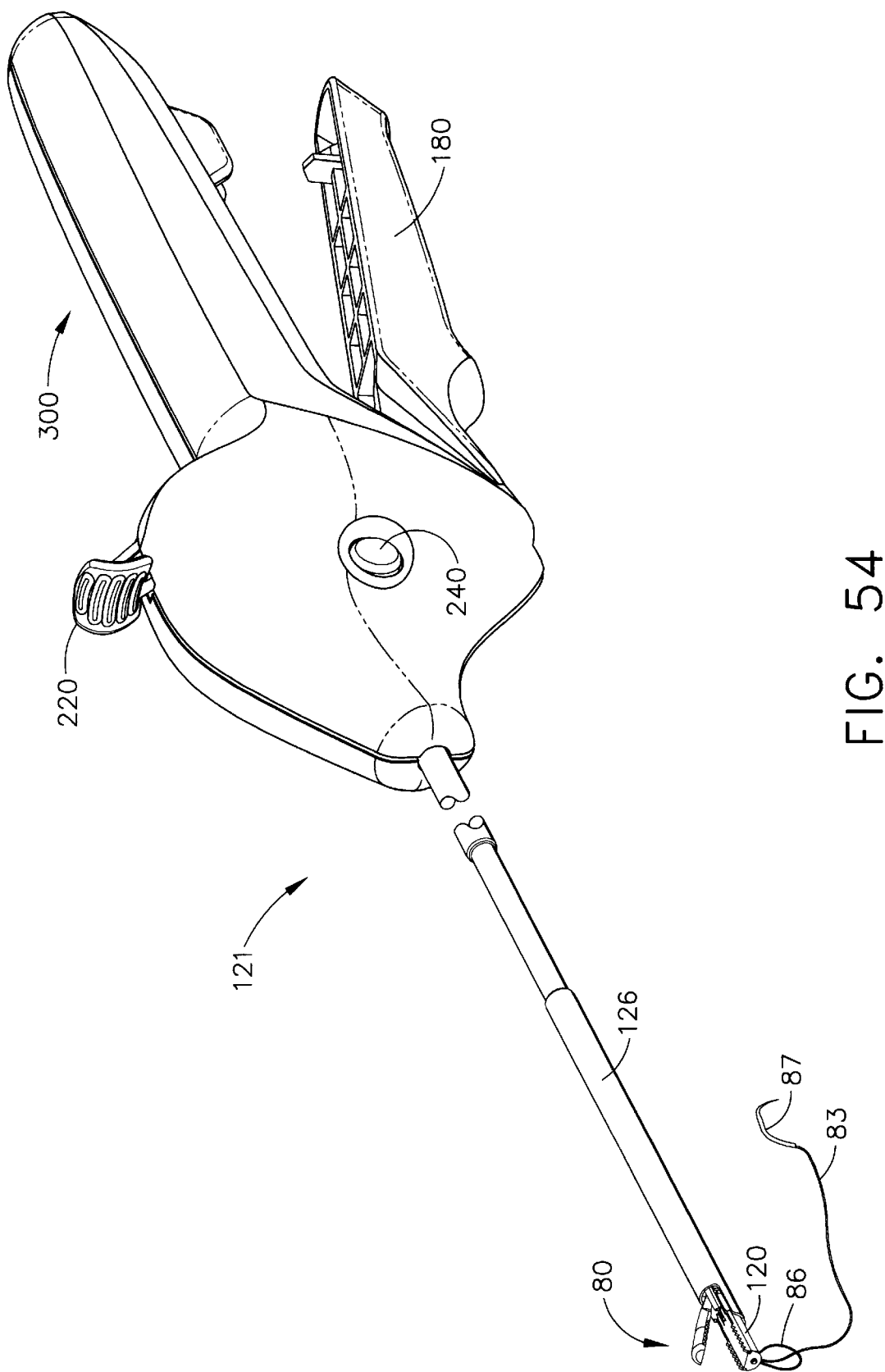
FIG. 54 is a perspective view of the surgical instrument of FIG. 51 in the configuration for when the distal portion is loaded with a suture cartridge assembly.
Figure 55:
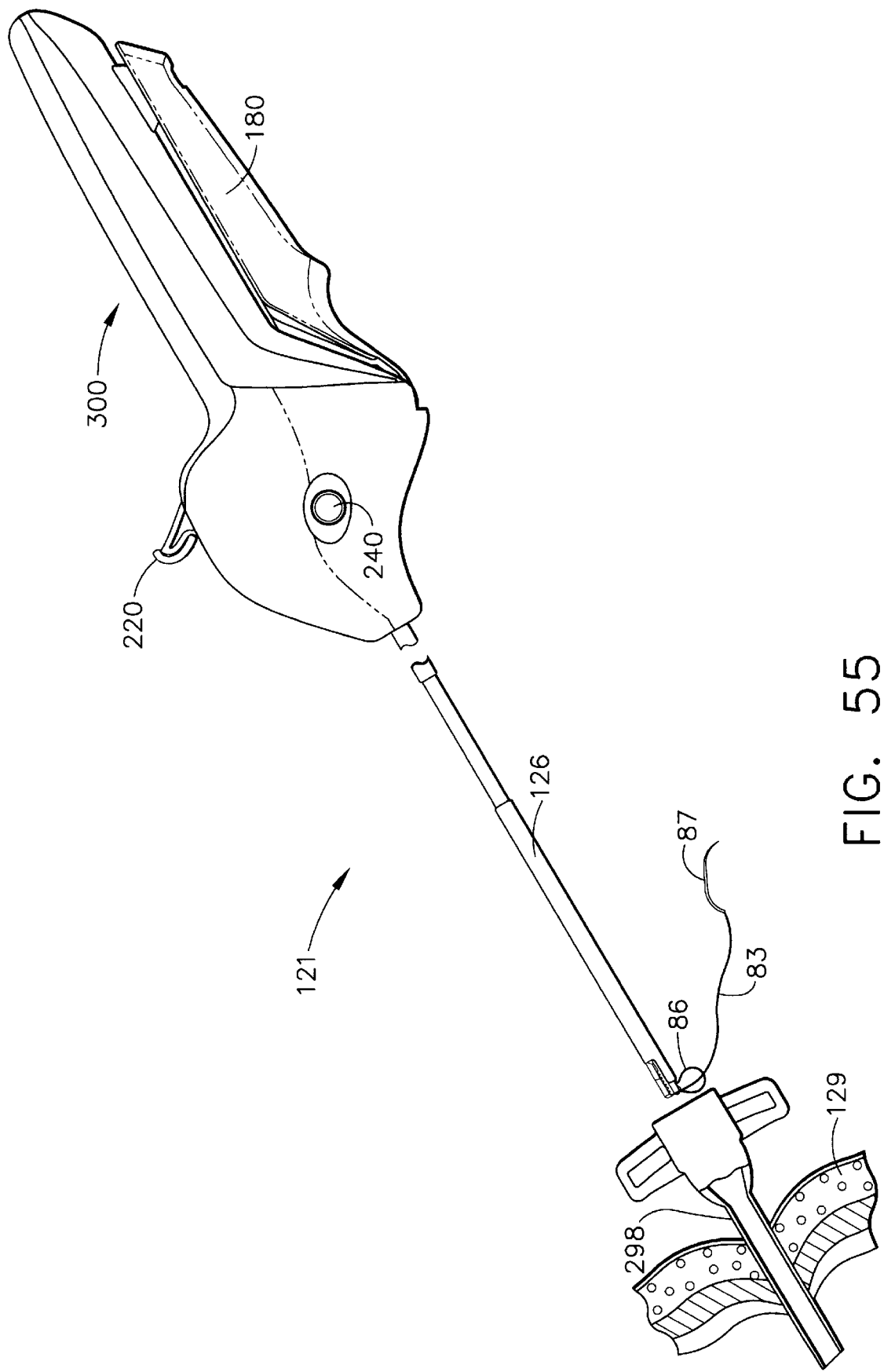
FIG. 55 is a side elevation of the surgical instrument of FIG. 51 shown being introduced into an endoscopic opening into the body.
Figure 56:
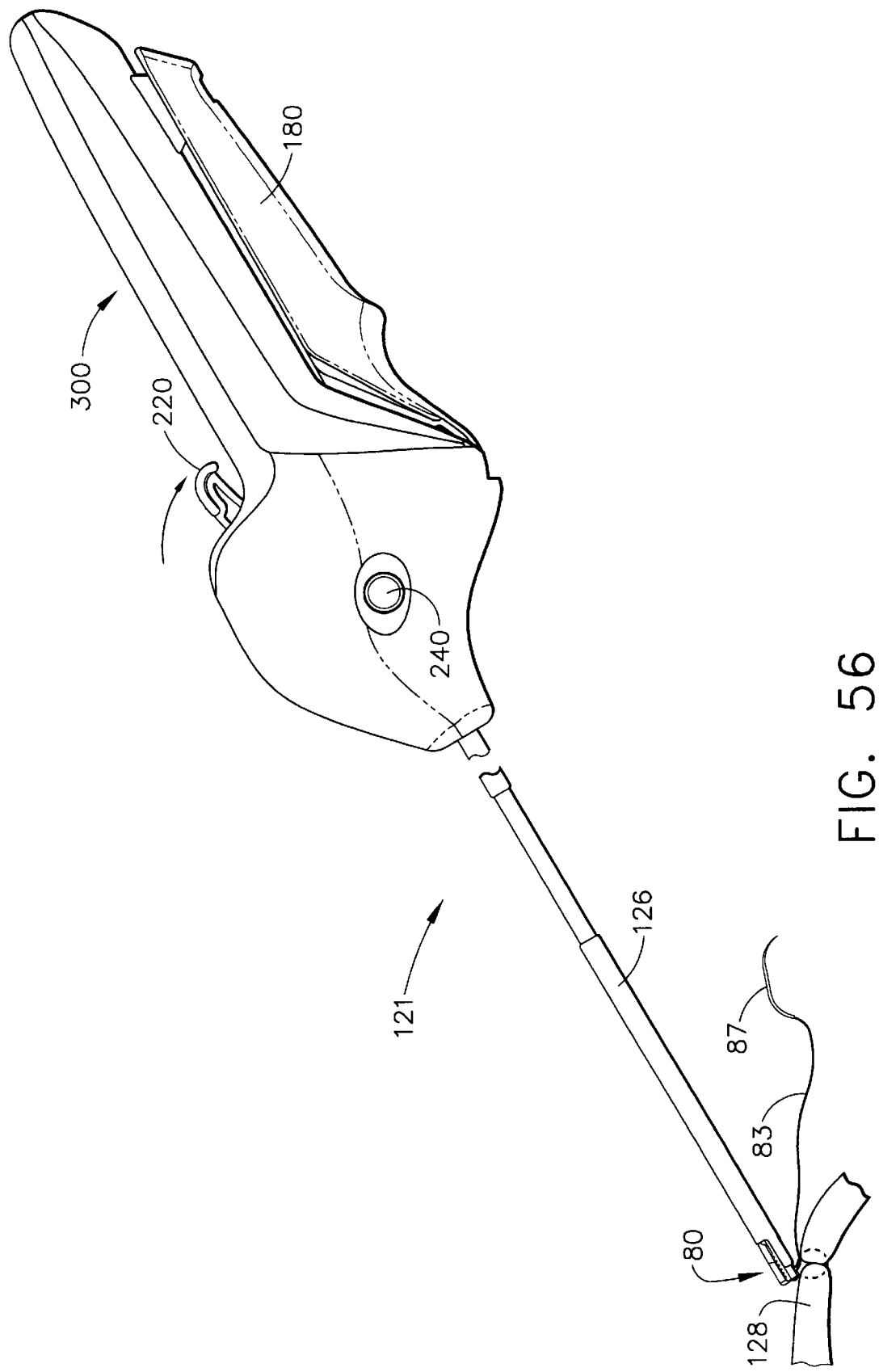
FIG. 56 is a side elevation of the surgical instrument of FIG. 51 after the lever has been actuated and the knot has been deployed into anatomical tissue.

FIGS. 51–56 depict the intended sequence of operation of the surgical instrument 121 and are described next. Turning again to FIG. 51, the instrument is shown in a configuration as it may be received prior to initial usage. As can be seen in FIG. 52 which correlates with FIG. 51, the cartridge carrier 120 is empty and the distal end of closure tube 126 is positioned longitudinally about halfway between its most distal and most proximal position, hereinafter referred to as the middle position. FIG. 53 depicts the surgical instrument in the load/unload configuration. The left and right release buttons 240 and 238 have been depressed simultaneously, and the trigger 180 has sprung open to the position shown, in turn, causing the closure tube 126 to retract in the proximal direction. The suture cartridge assembly 80 is shown ready for placement into the cartridge carrier 120, and the sequence depicted in FIGS. 43–45 using the load assist device 130 would take place next. In FIG. 54, the trigger 180 has been actuated to the middle position as shown and the closure tube 126 has moved distally to its middle position as depicted in FIG. 53. The suture cartridge assembly 80 is now captured in the cartridge carrier 120 and the instrument containing the cartridge may be withdrawn from the load assist device. The next step in the use of the instrument is to introduce the distal end into the anatomical body cavity as shown in FIG. 55, and since it is necessary for the grasping jaw 94 to be in its closed position for insertion through an endoscopic cannula 298, the surgeon's assistant may fully close the trigger 180 until it latches against grip 192 and is held there by trigger latch 281 before removing the instrument from the load assist device and handing it to the surgeon. This loading sequence is depicted in FIG. 46–49. Once the surgeon has introduced the distal portion of the instrument into the anatomical body cavity through the endoscopic cannula, the full actuation of the trigger will cause the release of the trigger from the grip, in turn allowing the closure tube 126 to retract proximally and the grasping jaw 94 to open. The surgical instrument may now be used for the grasping and manipulation of tissue (as in FIG. 37), the suture (as in FIG. 38), or the needle (as in FIG. 39). FIG. 56 shows the instrument as the knot is being deployed to fasten the tissue 128. The lever 220 has been actuated by the surgeon's thumb or finger in a downward arc until an internal stop is reached to deploy the knot. This actuation may be stopped at any point along this arc and the lever will maintain its position. This feature allows the surgeon to be able to manipulate and/or inspect the suture and the tissue it's affixed to for proper suture tensioning and placement of the knot. Once the lever 220 is fully actuated and the surgeon's thumb or finger is lifted off of it, the lever returns under spring force to the starting position. The instrument may then be withdrawn from the anatomical body cavity, with or without the trigger 180 in the closed position, and be readied for loading of a new suture cartridge assembly.

Figure 50:
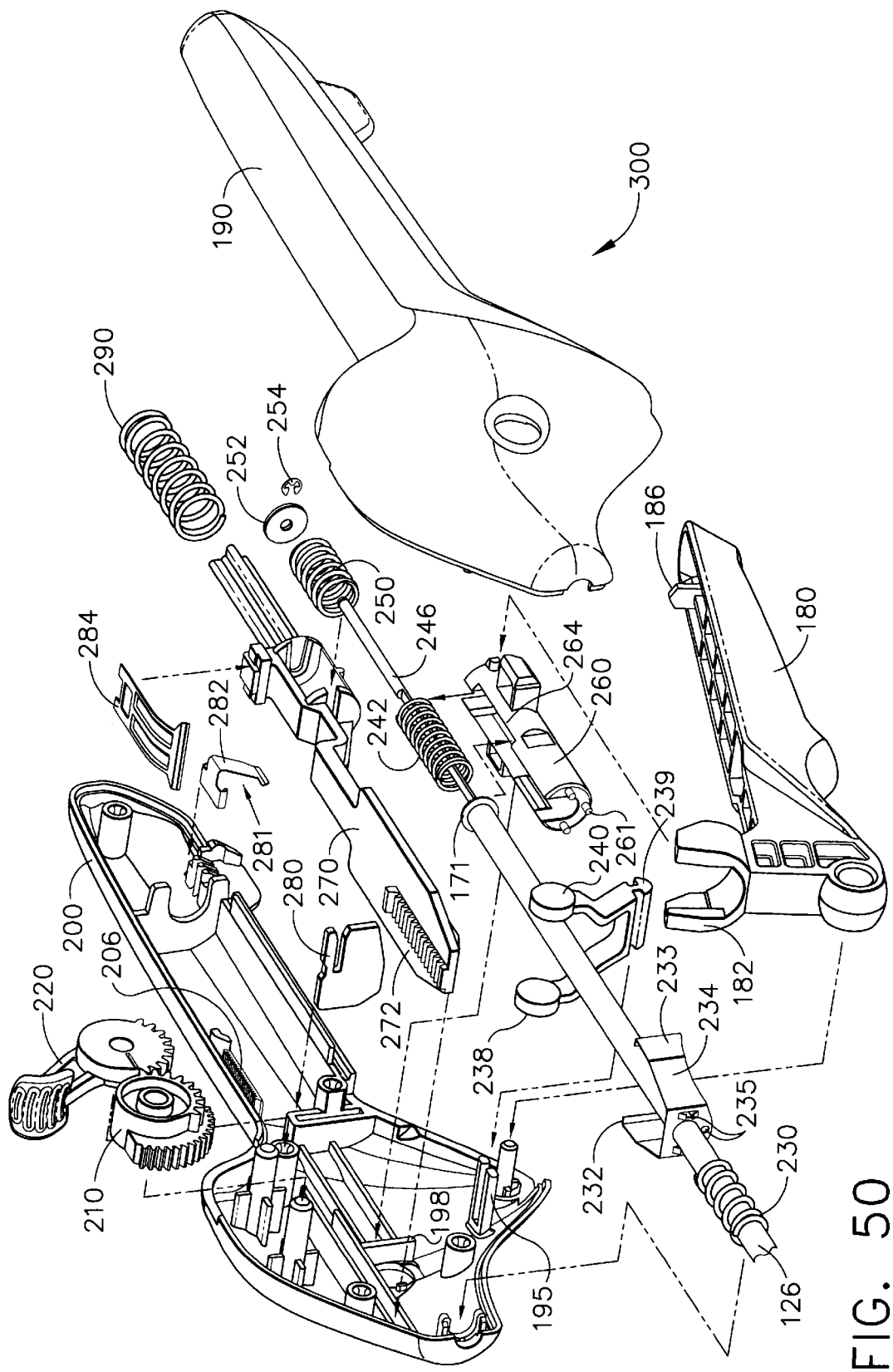
FIG. 50 is an exploded, perspective view of the components of the handle assembly for the preferred surgical instrument of this invention.

FIG. 50 is an exploded, perspective view of the components of the handle assembly 300 together with the closure tube 126. The outer shell of the grip 192 consists of a left grip cover 190 and a right grip cover 200, both made preferably of a rigid, medical grade plastic such as polycarbonate. These covers contain a plurality of bosses and ribs to support and align the components within. The trigger 180 and the lever 220 are supported between the left and right grips to move as described previously. A pinion 210, a rack 270, and a closure coupler 260 may be made of metal, but are preferably made of various types of injection molded, rigid, medical grade plastics. The following components of the handle assembly 300 may be made of plastics, but are preferably made of metal, such as a stainless steel: a base anchor 280, trigger latch spring 282, a leaf spring pawl 284, a lever spring 290, a tube spring 230, a tube latch 234, a coupler spring 242, a rack spring 250, a washer 252, a retaining ring 254, and a suture pull rod 246.

Figure 57:
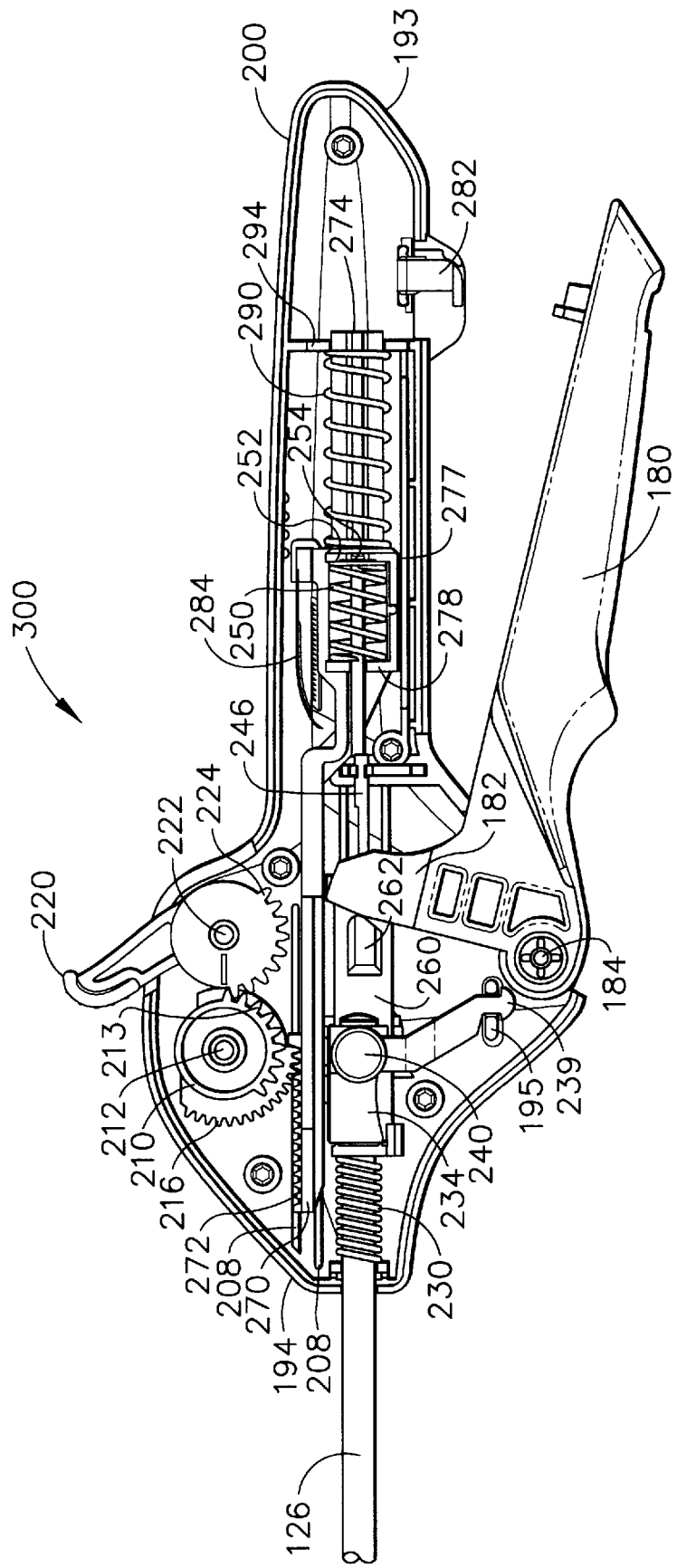
FIG. 57 is a side elevation of the interior of the handle assembly of the surgical instrument of FIG. 51 in the configurations depicted in both FIGS. 51 and 54.

Still referring to FIG. 50 and also now to FIG. 57, the components of the handle assembly 300 are visible and are in the operational configuration corresponding to FIGS. 51 and 54. The trigger 180 is in its middle position and is supported on a pivot boss 184 projecting off right grip cover 200. A trigger fork 182 bears against a left and a right push arm 262 and 263, respectively, of closure coupler 260 which is attached to closure tube 126 by a flange 171 (see FIG. 50) inserted in a coupler recess 264 (see FIG. 50). Coupler spring 242 is compressed between the flange and the proximal end of coupler recess 264 so that longitudinal force transmitted from the coupler to the closure tube is limited by the spring rate of the coupler spring. This is to insure that an excessive force is not applied to the jaw 157 by the distal end of the closure tube when the surgeon is attempting to grasp tissue or another object which does not permit the jaw to close fully. The described train of components is biased in the proximal direction by a partially compressed tube spring 230 which is captured on the proximal end of closure tube 126. The tube spring pushes off of the inside wall of the grip proximal end 193. Closure coupler 260 is held in its middle, longitudinal position by tube latch 234 and they are attached together by three coupler posts 261 pressed into three holes 235 of the tube latch 234 (see FIG. 50). Tube latch 234 is sprung open transversely so that a tube latch right end 232 engages with a right latch rib 198 projecting off right grip cover 200, and similarly, a tube latch left end 233 engages with a mirrored left latch rib (not shown) in left grip cover 190. Right and left release buttons, 238 and 240, are positioned over right and left tube latch ends, 232 and 233 respectively. Release buttons 238 and 240 are joined together in a "wishbone" manner to a "dovetail-shaped" button anchor 239 which inserts into a right button retainer 195 and a mirrored left button retainer (not shown) extending off of right and left grip covers, 200 and 190, respectively.

Still referring to FIG. 57, lever 220 is shown in its start position and is supported on a lever pivot boss 222 projecting off right grip cover 200. A plurality of lever gear teeth 224 mesh with a plurality of pinion minor gear teeth 213 of pinion 210 which is supported on a pinion pivot boss 212 projecting also off right grip cover 200. A plurality of pinion major gear teeth 216 mesh with a plurality of rack gear teeth 272 of rack 270 which is constrained to move longitudinally between grip cover ribs 208 projecting off of left and right grip covers 190 and 200. Lever spring 290 is captured on a proximal end 274 of the rack 270 and is partially compressed in order to exert an initial separating force between a rack spring chamber proximal end 277 of the rack and two grounding ribs, 295 and 294, projecting off left and right grip covers 190, 200. These grounding ribs are "C-shaped" and extend to the center axis of the handle assembly 300. Together they form a hole so that clearance for the distal end 274 of the rack 270 is provided to allow the longitudinal movement of the rack in the proximal direction. The force of the preloaded lever spring 290 biases the rack in the distal direction and is transmitted through the drive components described to the lever 220, thus biasing the lever to remain in its start position.

Figure 58:
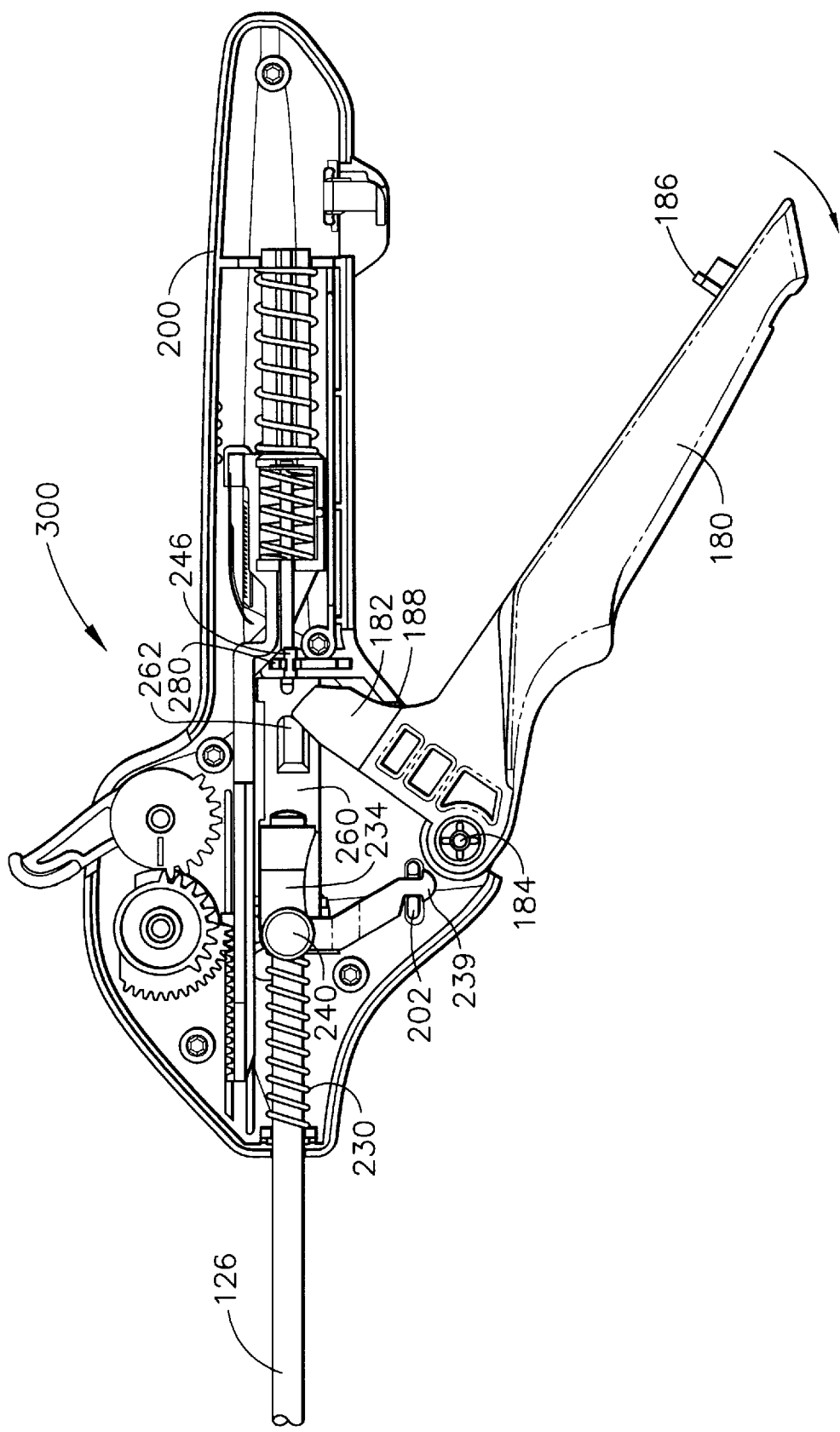
FIG. 58 is a side elevation of the interior of the handle assembly of the surgical instrument of FIG. 51 in the load/unload configuration depicted in FIG. 53.

Referring now to FIG. 58, the handle assembly 300 is shown in the operational configuration corresponding with FIG. 53 for when the surgical instrument may be loaded or unloaded with suture cartridge assembly 80. The trigger 180 is swung fully away from the longitudinal axis of handle assembly 300 due to the release of the closure coupler 260. The surgeon or the surgeon's assistant will have obtained this handle configuration by simultaneously squeezing the left and right release buttons, 240 and 238, with their thumb and an opposing finger, causing the compression of the tube latch 234, in turn causing the tube latch 234 to disengage from the right and left latch ribs, 198 and 199. Tube spring 230 exerts a force in the proximal direction on the end of the closure coupler 260. The closure coupler 234, the tube latch 234, and the closure tube 121 immediately move proximally, forcing the trigger 180 to open fully. The trigger opening is limited by the trigger forks 182 hitting against a trigger stop 188 of the covers, 190 and 200. In order for the trigger to open, the user must not be holding the trigger 180 while the release buttons, 238 and 240, are compressed. This feature specifically is intended to make the retraction of the closure tube 126 a deliberate step while still being one-handed, because it is desirable to prevent the accidental release of a suture cartridge assembly 80 into the body cavity.

Once the spent or "fired" suture cartridge assembly is unloaded from the cartridge carrier 120 and a new one is loaded according to the steps depicted in FIGS. 43–49, the handle assembly is put into the "ready to deploy" mode as shown in FIG. 59 by squeezing trigger 180 far enough to force the reengagement of tube latch 234 with the left and right latch ribs, 199 and 198, thus repositioning the closure tube 126 into a position where the suture cartridge assembly 80 is captured in the cartridge carrier 120. When this is achieved, the surgeon may choose to leave the trigger 180 in this position during the actuation of the lever 220, or to close the trigger completely and allow it to latch against the grip, or to hold the trigger anywhere between the aforementioned positions.

In FIG. 60, the case is shown for when the lever 220 has been fully actuated while the trigger 180 has been partially squeezed, but not far enough for trigger hook 186 to latch with a trigger latch spring 282. The downward movement of the lever 220, via the series of gear interactions already described, has caused the rack 270 to move longitudinally in the proximal direction and the lever spring 290 to compress. The rack spring 250 contained in the rack spring chamber 276 has likewise moved proximally and transmits a longitudinal force in the proximal direction against washer 252 which abuts against retaining ring 254 which is attached to suture pull rod 246. The suture pull rod, in turn, is attached at its distal end to the hook 127 (FIG. 33) which engages with the proximal end of the suture filament. When the suture pull rod is moved proximally, the knot is deployed in a manner substantially similar to that illustrated in FIGS. 11–15. The rack spring 250, therefore, acts as a force-limiting means in that the total force transmitted from the rack 270 to the suture pull rod 246 is equal to the pre-loaded force of the rack spring added to the product of the spring rate of the rack spring 250 and the distance it has been compressed between the rack spring chamber distal end 276 and the washer 252. The force-limiting feature of this invention helps to prevent the excessive tensioning of the suture filament, in which case the filament would break before the knot could be fully deployed. The total force is transmitted, however, only when the resistive force of the suture pull rod 246 equals or exceeds the pre-loaded force of the rack spring 250. This resistive force varies primarily with the tension and angle of tensioning of the suture filament distal end 83 (FIG. 56) as applied by the surgeon during approximation and fastening of the tissue. The maximum resistive force typically occurs at the instant the knot converts to a non-slipping knot, as shown in FIGS. 7, 8. It is important, therefore, that the rack spring 250 be sized and pre-loaded to transmit a sufficient longitudinal force for knot conversion without the spring collapsing to its solid height, in which case the surgeon may exert an excessive force to the lever 220 and cause the suture proximal filament 33 to break. The rack spring 250 should not be sized and pre-loaded to a condition where the force required to compress it an additional amount nears or exceeds the suture filament tensile strength because then the force-limiting feature could not be used to prevent breaking of the suture filament. During the transmission of the forces as described, the cartridge carrier 120 is grounded to the grip 192 by attachment to base anchor 280 inserted into a recess 281 on the inner wall of right grip cover 200 (see FIG. 50).

Still referring to FIG. 60, the "T-shaped" leaf spring pawl 284 can be seen mounted to rack 270. During the actuation of the lever 220, the transverse arms of the leaf spring pawl engage with a plurality of teeth 206 molded onto the inner surfaces of the left and right grip covers, 190 and 200 (see FIG. 50) so that the rack can maintain its longitudinal position at numerous discrete points between the stating and stopping positions of the lever if the surgeon were to release pressure from the lever. The lever must be fully actuated before the leaf spring pawl has traveled beyond the end of the molded teeth 206, thereby the pawl disengages from the teeth and springs to a position to allow the return of the lever to the staring position. The lever must then be released by the surgeon so that the rack 270 can move distally due to the force of the lever spring 290, causing the lever to return to its start position. This lever holding feature is well-known in the art for its use in other surgical devices such as skin staplers.

The handle assembly described is the preferred embodiment, but it may be appreciated that other grip shapes and mechanisms within this assembly are possible for accomplishing the desired functions. For example, the handle assembly may have a "pistol grip" or incorporate openings into the grip and trigger for insertion of the thumb and an opposing finger. In addition, the distal portion of this surgical instrument could be made to rotate about its longitudinal axis while the handle assembly was held stationary, with or without a locking mechanism for this rotation. The surgical instrument described can be made to be single patient-use disposable, reusable, or a combination of the two, depending primarily on the materials chosen and the method of assembly.

The different embodiments of this invention are representative of the preferred embodiments of the invention. These embodiments are merely illustrative. The scope of the invention should not be construed to be limited by these embodiments, or any other particular embodiments which may come to mind to those skilled in this art. Instead, the reader must refer to the claims which appear below to determine the scope of the invention.

What is claimed is:

1. A surgical instrument for forming a fully tied knot to fasten bodily tissue during a surgical procedure, said instrument comprising:
   a) a suture cartridge at a distal end of said instrument, said cartridge containing a suture filament configured into a partially tied knot at a distal end of said suture filament;
   b) a cartridge carrier at the instrument distal end for receiving said suture cartridge;
   c) a grasping jaw facing said suture cartridge in said cartridge carrier, said grasping jaw moveable from an open position spaced from said suture cartridge to a closed position adjacent said suture cartridge;
   d) a handle assembly spaced from said suture cartridge and located at a proximal end of said instrument, said handle assembly having:
      i) a grip for manipulating said instrument,
      ii) a first actuator for effecting the movement of the grasping jaw from the open position to the closed position, and
      iii) a second actuator operatively connected to a proximal end of said suture filament for pulling the filament proximal end proximally so as to form said fully tied knot from said partially tied knot to fasten the bodily tissue; and
   e) a closure tube coupling said cartridge carrier to said handle assembly, said closure tube moveable from a proximal position wherein said grasping jaw is in the open position to a distal position wherein said grasping jaw is in the closed position in response to actuation of said first actuator.

2. The instrument of claim 1 wherein said suture cartridge is loaded into said cartridge carrier when said closure tube is in its proximal position, and said suture cartridge is secured in said cartridge carrier when said closure tube is moved to a middle position between its proximal and distal positions.

3. The instrument of claims 1 further comprising a first biasing element cooperable with said second actuator and the proximal end of said suture filament for preventing said suture filament from breaking when said second actuator is actuated so as to form said fully tied knot.

4. The instrument of claim 3 further comprising a second biasing element cooperable with said first actuator for providing overload protection when said first actuator is actuated so as to move said closure tube from its proximal position to its distal position.

5. The instrument of claim 1 wherein said first actuator is a trigger pivotally mounted on said handle assembly, said first actuator is moveable from a first trigger position spaced from said grip to a second trigger position adjacent said grip, wherein when said first actuator is in its first trigger position, said closure tube is in its proximal position, and when said first actuator is in its second trigger position, said closure tube is in its distal position.

6. The instrument of claim 5 wherein said first actuator is moveable to a third trigger position between said first and second trigger positions, and when said first actuator is in its third trigger position, said closure tube is in its middle position.

7. The instrument of claim 5 wherein said second actuator is a lever pivotally mounted on said handle assembly, and said lever is pivoted from a first lever position to a second lever position so as to pull the filament end proximally for forming said fully tied knot.

8. The instrument of claim 7 wherein said handle assembly of said instrument is adapted for one-handed operation for actuating said trigger and said lever with a single hand when said grip is placed in the palm of a user's hand.

9. The instrument of claim 8 wherein said trigger is biased toward its first trigger position, said closure tube is biased toward its proximal position, and said lever is biased toward its first lever position.

10. The instrument of claim 9 further comprising a release button protruding from said handle assembly, said release button cooperable with said closure tube and said trigger, wherein when said release button is depressed inwardly toward said handle assembly, and said trigger is in its second or third trigger positions, said trigger moves to its first trigger position.

11. The instrument of claim 7 wherein said suture cartridge has a hook slot therein, the proximal end of said suture filament traverses said hook slot, and said lever is connected to a pinion housed inside said handle assembly.

12. The instrument of claim 11 further comprising a rack housed inside said handle assembly cooperable with said pinion, and a suture pull rod connected to said rack, said suture pull rod extending from said handle assembly to said cartridge carrier, said suture pull rod having a hook at a distal end thereof extending through said hook slot of said suture cartridge, wherein when said lever is pivoted from said first lever position to said second position, said pinion moves said rack and said suture pull rod connected thereto proximally, and said hook on said suture pull rod pulls the proximal end of said suture filament traversing said hook slot in said suture cartridge proximally so as to form said fully tied knot from said partially tied knot.

* * * * *